United States Patent
Toda

(10) Patent No.: US 6,691,577 B1
(45) Date of Patent: Feb. 17, 2004

(54) ULTRASONIC MOVING-SPEED MEASURING SYSTEM

(76) Inventor: Kohji Toda, 1-49-18 Futaba, Yokosuka (JP), 239-0814

(*) Notice: Subject to any disclaimer, the term of this patent is extended or adjusted under 35 U.S.C. 154(b) by 0 days.

(21) Appl. No.: 10/287,013

(22) Filed: Nov. 1, 2002

(51) Int. Cl.$^7$ ............................................. G01S 15/58
(52) U.S. Cl. ......................................... 73/602; 367/90
(58) Field of Search .................. 73/602, 627, 628, 73/629, 632, 642, 593; 367/89, 90, 91, 101, 102

(56) References Cited

U.S. PATENT DOCUMENTS

| | | | | |
|---|---|---|---|---|
| 4,674,334 A | * | 6/1987 | Chimenti et al. | 73/627 |
| 4,830,016 A | * | 5/1989 | Tamano et al. | 600/455 |
| 5,097,453 A | * | 3/1992 | Kobayashi et al. | 367/91 |
| 5,228,347 A | * | 7/1993 | Lowell et al. | 73/861.28 |
| 5,239,516 A | * | 8/1993 | Kimura | 367/91 |
| 5,441,052 A | * | 8/1995 | Miyajima | 600/455 |
| 6,212,129 B1 | * | 4/2001 | Nussbaumer et al. | 367/89 |
| 6,564,649 B1 | * | 5/2003 | Toda | 73/861.26 |

FOREIGN PATENT DOCUMENTS

JP 2001074760 A * 3/2001 ............ G01P/5/00

* cited by examiner

Primary Examiner—Hezron Williams
Assistant Examiner—Rose M. Miller

(57) ABSTRACT

An ultrasonic moving-speed measuring system comprises a piezoelectric substrate, a thickness-vibration mode transducer, an interdigital transducer, and a signal analyzer. The piezoelectric substrate, the thickness-vibration mode transducer, and the interdigital transducer form a transducing assembly. When an input electric signal with a carrier frequency is applied to the thickness-vibration mode transducer, a longitudinal wave is radiated into a medium that is in touch with the bottom of the transducing assembly. If the longitudinal wave is reflected at a material in the medium, a delayed electric signal with a Doppler frequency is detected at the interdigital transducer via a mode conversion from a reflected longitudinal wave to a leaky Lamb wave. The moving speed of the material is sensed at the signal analyzer in terms of a difference between the carrier- and Doppler frequencies.

22 Claims, 31 Drawing Sheets rotating direction

US 6,691,577 B1

ULTRASONIC MOVING-SPEED MEASURING SYSTEM

BACKGROUND OF THE INVENTION

1. Field of the Invention

The present invention relates to an ultrasonic system for measuring a moving speed of a material in a medium, or a flowing speed of a liquid by making use of the Doppler effect.

2. Description of the Prior Art

The Doppler effect is available for measuring a moving speed of a material in a medium, or a flowing speed of a liquid. Conventional devices popularly use two thickness-vibration mode transducers; one acts as an input transducer generating an ultrasound vertical to a piezoelectric substrate surface, on which the input transducer is formed; the other acts as an output transducer detecting a reflected ultrasound vertical to a piezoelectric substrate surface, on which the output transducer is formed. Accordingly, it is mechanically difficult to determine a situation of the output transducer to the input transducer. In addition, conventional devices have some problems on measurement accuracy, response time, difficulty in use, and durability. Moreover, conventional devices are easy to be affected by a change in circumstances, such as temperature, pressure, and so on.

SUMMARY OF THE INVENTION

An object of the present invention is to provide an ultrasonic moving-speed measuring system with a high sensitivity.

Another object of the present invention is to provide an ultrasonic moving-speed measuring system capable of operating at a high frequency.

Another object of the present invention is to provide an ultrasonic moving-speed measuring system excellent in measurement accuracy, response time, durability, and manufacturing.

Another object of the present invention is to provide an ultrasonic moving-speed measuring system capable of canceling a change in circumstances such as temperature, pressure, and so on.

Another object of the present invention is to provide an ultrasonic moving-speed measuring system capable of low electric power consumption.

A still other object of the present invention is to provide an ultrasonic moving-speed measuring system easy in use and having a small size which is very light in weight and has a simple structure.

According to one aspect of the present invention there is provided an ultrasonic moving-speed measuring system comprising (1) a piezoelectric substrate, (2) a first electrode formed on an upper end surface of the piezoelectric substrate, (3) a second electrode formed on a lower end surface of the piezoelectric substrate, (4) an interdigital transducer formed on the upper end surface of the piezoelectric substrate, and (5) a signal analyzer. The first electrode and the second electrode that is located at the corresponding position with the first electrode form a thickness-vibration mode transducer. The piezoelectric substrate, the thickness-vibration mode transducer, and the interdigital transducer form a transducing assembly.

When an input electric signal with a carrier frequency, approximately equal to the center frequency for operating the thickness-vibration mode transducer, is applied to the thickness-vibration mode transducer, a longitudinal wave is radiated into a medium that is in touch with the bottom of the transducing assembly. If the longitudinal wave is reflected at a material in the medium, a delayed electric signal with a Doppler frequency is detected at the interdigital transducer via a mode conversion from a reflected longitudinal wave to a leaky Lamb wave. A moving speed of the material is sensed at the signal analyzer in terms of a difference between the carrier- and Doppler frequencies.

According to another aspect of the present invention there is provided an interdigital transducer having a dispersive electrode-pattern.

According to another aspect of the present invention there is provided an interdigital transducer having an arch-shaped electrode-pattern with a concentric center at a coincident situation with the center of the first electrode.

According to another aspect of the present invention there is provided a counter electrode formed on the lower end surface of the piezoelectric substrate and located at the corresponding position with the interdigital transducer.

According to another aspect of the present invention there is provided a signal generator generating an input electric signal $E_i$ ($i=1, 2, \ldots$, or n) with a carrier frequency $F_{0i}$ ($i=1, 2, \ldots$, or n) in response to a distance $D_i$ ($i=1, 2, \ldots$, or n), respectively, between the transducing assembly and the material, in order to make the interdigital transducer n) via a mode conversion from a reflected longitudinal wave with a reflection angle $\alpha_i$ ($i=1, 2, \ldots$, or n) to a leaky Lamb wave.

According to another aspect of the present invention there is provided a first electrode made of two comb-shaped electrodes making together an interdigital arrangement. In this time, the ratio of the interdigital periodicity of the interdigital arrangement to the thickness of the piezoelectric substrate is smaller than five times the ratio of the longitudinal wave velocity in the medium to the leaky Lamb wave velocity in the piezoelectric substrate.

According to another aspect of the present invention there is provided a nonpiezoelectric film, with which the bottom of the transducing assembly is covered.

According to another aspect of the present invention there is provided a piezoelectric substrate made of a piezoelectric ceramic thin plate. In this time, the polarization axis thereof is parallel to the thickness direction thereof.

According to another aspect of the present invention there is provided a piezoelectric substrate made of a piezoelectric polymer film.

According to another aspect of the present invention there is provided a piezoelectric substrate made of a piezoelectric single crystal.

According to another aspect of the present invention there is provided an ultrasonic moving-speed measuring system comprising (1) a piezoelectric substrate, (2) a first interdigital transducer formed on an upper end surface of the piezoelectric substrate, (3) a second interdigital transducer having the same electrode pattern as the first interdigital transducer and formed on the upper end surface of the piezoelectric substrate, (4) a first electrode formed on the upper end surface of the piezoelectric substrate and located between the first- and second interdigital transducers, a second electrode formed on a lower end surface of the piezoelectric substrate and located at the corresponding position with the first electrode, and a signal analyzer. The first- and second electrodes form a thickness-vibration mode transducer. The piezoelectric substrate, the thickness-vibration mode transducer, and the first- and second interdigital transducers form a transducing assembly.

When an input electric signal with a carrier frequency, approximately equal to the center frequency for operating the thickness-vibration mode transducer, is applied to the thickness-vibration mode transducer, a longitudinal wave is radiated into a medium that is in touch with the bottom of the transducing assembly. If the longitudinal wave is reflected at a material in the medium, a first delayed electric signal with a first Doppler frequency is detected at the first interdigital transducer via a mode conversion from a first reflected longitudinal wave to a first leaky Lamb wave, and at the same time, a second delayed electric signal with a second Doppler frequency is detected at the second interdigital transducer via a mode conversion from a second reflected longitudinal wave to a second leaky Lamb wave. A moving direction and a moving speed of the material is sensed at the signal analyzer in terms of a difference between the carrier frequency and a larger one of the first- and second Doppler frequencies.

According to another aspect of the present invention there are provided first- and second interdigital transducers, wherein an intersecting line on each finger-center of the finger overlap-zone of the first interdigital transducer and that of the second interdigital transducer overlap each other.

According to another aspect of the present invention there are provided first- and second interdigital transducers having a dispersive electrode-pattern, respectively.

According to another aspect of the present invention there are provided first- and second interdigital transducers having an arch-shaped electrode-pattern, respectively, and making a pair with a concentric center at a coincident situation with the center of the first electrode.

According to another aspect of the present invention there are provided first- and second counter electrodes. The first counter electrode is formed on the lower end surface of the piezoelectric substrate and located at the corresponding position with the first interdigital transducer. The second counter electrode is formed on the lower end surface of the piezoelectric substrate and located at the corresponding position with the second interdigital transducer.

According to another aspect of the present invention there is provided a signal generator generating an input electric signal $E_i$ (i=1, 2, ..., or n) with a carrier frequency $F_{0i}$ (i=1, 2, ..., or n) in response to a distance $D_i$ (i=1, 2, ..., or n), respectively, between the transducing assembly and the material. The use of such the signal generator makes the first interdigital transducer detect a first delayed electric signal with a first Doppler frequency $F_{fi}$ (i=1, 2, ..., or n) via a mode conversion from a first reflected longitudinal wave with a reflection angle $\alpha_i$ (i=1, 2, ..., or n) to a first leaky Lamb wave, and at the same time, makes the second interdigital transducer detect a second delayed electric signal with a second Doppler frequency $F_{si}$ (i=1, 2, ..., or n) via a mode conversion from a second reflected longitudinal wave with the reflection angle $\alpha_i$ to a second leaky Lamb wave.

According to another aspect of the present invention there is provided an ultrasonic moving-speed measuring system comprising (1) a piezoelectric substrate, (2) a first interdigital transducer, (3) a second interdigital transducer, (4) a third interdigital transducer, (5) a first electrode formed on the upper end surface of the piezoelectric substrate, (6) a second electrode formed on a lower end surface of the piezoelectric substrate, and (7) a signal analyzer. The first-, second-, and third interdigital transducers have the same electrode patterns as one another, and are formed on the upper end surface of the piezoelectric substrate such that they together make a triangle. The first electrode is formed among the first-, second-, and third interdigital transducers on the upper end surface of the piezoelectric substrate. The second electrode formed on the lower end surface of the piezoelectric substrate is located at the corresponding position with the first electrode. The first- and second electrodes form a thickness-vibration mode transducer. The piezoelectric substrate, the thickness-vibration mode transducer, and the first-, second-, and third interdigital transducers form a transducing assembly.

When an input electric signal with a carrier frequency, in a frequency band-width of ±6 dB from the center frequency for operating the thickness-vibration mode transducer, is applied to the thickness-vibration mode transducer, a longitudinal wave is radiated into a medium that is in touch with the bottom of the transducing assembly. If the longitudinal wave is reflected at a material in the medium, a first delayed electric signal with a first Doppler frequency is detected at the first interdigital transducer via a mode conversion from a first reflected longitudinal wave to a first leaky Lamb wave, and a second delayed electric signal with a second Doppler frequency is detected at the second interdigital transducer via a mode conversion from a second reflected longitudinal wave to a second leaky Lamb wave, and then a third delayed electric signal with a third Doppler frequency is detected at the third interdigital transducer via a mode conversion from a third reflected longitudinal wave to a third leaky Lamb wave. A moving direction and a moving speed of the material is sensed at the signal analyzer in terms of a combination of a first difference between the carrier frequency and the first Doppler frequency, a second difference between the carrier frequency and the second Doppler frequency, and a third difference between the carrier frequency and the third Doppler frequency.

According to another aspect of the present invention there are provided first-, second-, and third interdigital transducers, wherein a first intersecting line on each finger-center of the finger overlap-zone of the first interdigital transducer, a second intersecting line on each finger-center of the finger overlap-zone of the second interdigital transducer, and a third intersecting line on each finger-center of the finger overlap-zone of the third interdigital transducer meet one another at the center of the first electrode.

According to another aspect of the present invention there are provided first-, second-, and third interdigital transducers having a dispersive electrode-pattern, respectively.

According to another aspect of the present invention there are provided first-, second-, and third interdigital transducers having an arch-shaped electrode-pattern, respectively, and making a set with a concentric center at a coincident situation with the center of the first electrode.

According to other aspect of the present invention there are provided first-, second-, and third counter electrodes. The first counter electrode is formed on the lower end surface of the piezoelectric substrate and located at the corresponding position with the first interdigital transducer. The second counter electrode is formed on the lower end surface of the piezoelectric substrate and located at the corresponding position with the second interdigital transducer. The third counter electrode is formed on the lower end surface of the piezoelectric substrate and located at the corresponding position with the third interdigital transducer.

According to a further aspect of the present invention there is provided a signal generator generating an input electric signal $E_i$ (i=1, 2, ..., or n) with a carrier frequency $F_{0i}$ (i=1, 2, ..., or n) in response to a distance $D_i$ (i=1, 2, ..., or n), respectively, between the transducing assembly and the material. The use of such the signal generator makes the first interdigital transducer detect a first delayed electric signal with a first Doppler frequency $F_{fi}$ (i=1, 2, ..., or n) via a mode conversion from a first reflected longitudinal wave with a reflection angle $\alpha_i$ (i=1, 2, ..., or n) to a first leaky Lamb wave, and makes the second interdigital transducer detect a second delayed electric signal with a second Doppler frequency $F_{si}$ (i=1, 2, ..., or n) via a mode conversion from a second reflected longitudinal wave with the reflection angle $\alpha_i$ to a second leaky Lamb wave, and then, makes the third interdigital transducer detect a third delayed electric signal with a third Doppler frequency $F_{ti}$ (i=1, 2, ..., or n) via a mode conversion from a third reflected longitudinal wave with the reflection angle $\alpha_i$ to a third leaky Lamb wave.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
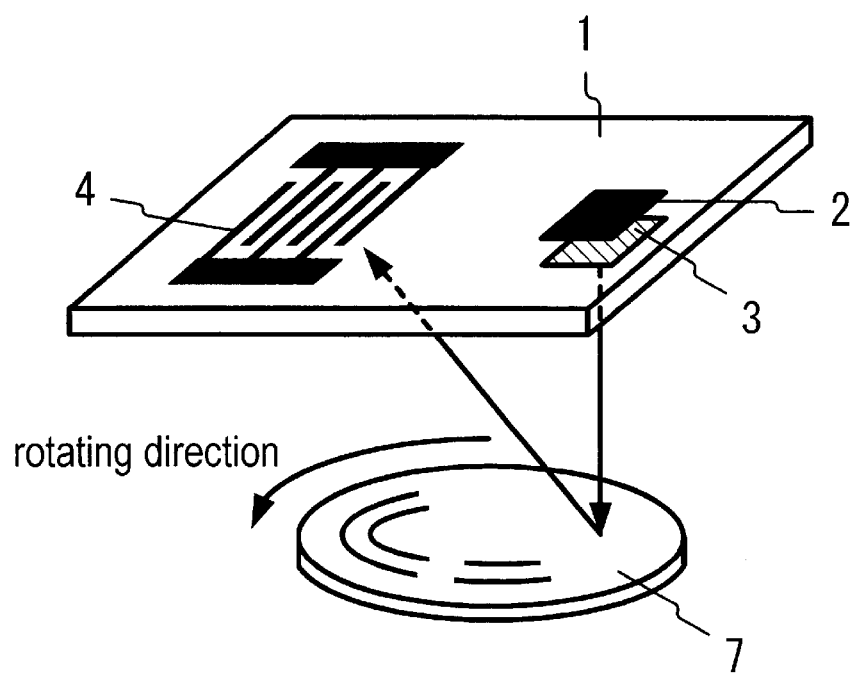
FIG. 1 shows a schematic illustration of an ultrasonic moving-speed measuring system according to a first embodiment of the present invention.

FIG. 1 shows a schematic illustration of an ultrasonic moving-speed measuring system according to a first embodiment of the present invention. The ultrasonic moving-speed measuring system comprises piezoelectric substrate 1, first electrode 2, second electrode 3, and interdigital transducer 4, and then, further comprises signal generator 5, and signal analyzer 6, which are not drawn in FIG. 1. Piezoelectric substrate 1, of which the polarization axis is parallel to the thickness direction thereof, is made of a ceramic thin plate with a dimension of 155 $\mu$m in thickness. It is possible to replace piezoelectric substrate 1 by a piezoelectric polymer film. First electrode 2 and interdigital transducer 4, made of an aluminum thin film, respectively, are formed on an upper end surface of piezoelectric substrate 1. Second electrode 3, made of an aluminum thin film, is formed on a lower end surface of piezoelectric substrate 1, and located at the corresponding position with first electrode 2. First electrode 2 and second electrode 3 have a rectangular plate-shape, respectively, and they together form a thickness-vibration mode transducer. Piezoelectric substrate 1, the thickness-vibration mode transducer, and interdigital transducer 4 form a transducing assembly. When sensing, for example, a rotating speed (S) of rotor 7 that is rotating in accordance with the curved arrow in water, the bottom of the transducing assembly is kept in contact with water. Thus, the ultrasonic moving-speed measuring system has a small size that is very light in weight and has a simple structure.

Figure 2:
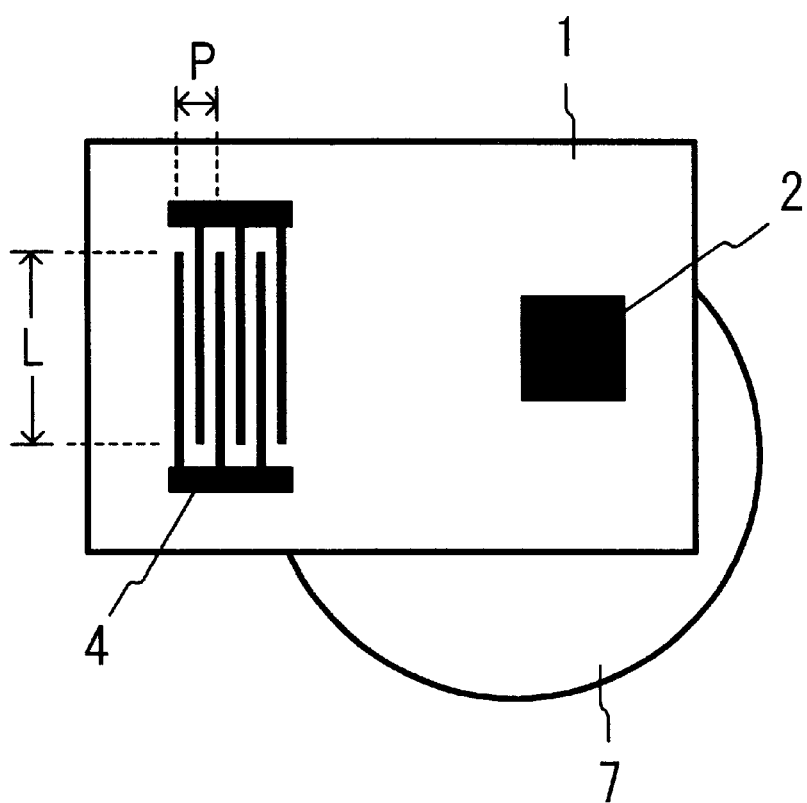
FIG. 2 shows a top plan view of the transducing assembly in FIG. 1 and rotor 7.

FIG. 2 shows a top plan view of the transducing assembly in FIG. 1 and rotor 7. Second electrode 3 is not drawn in FIG. 2. Interdigital transducer 4 has ten electrode-finger pairs, a finger-overlap length (L) of 10 mm, and an interdigital periodicity (P) of 320 μm.

Figure 3:
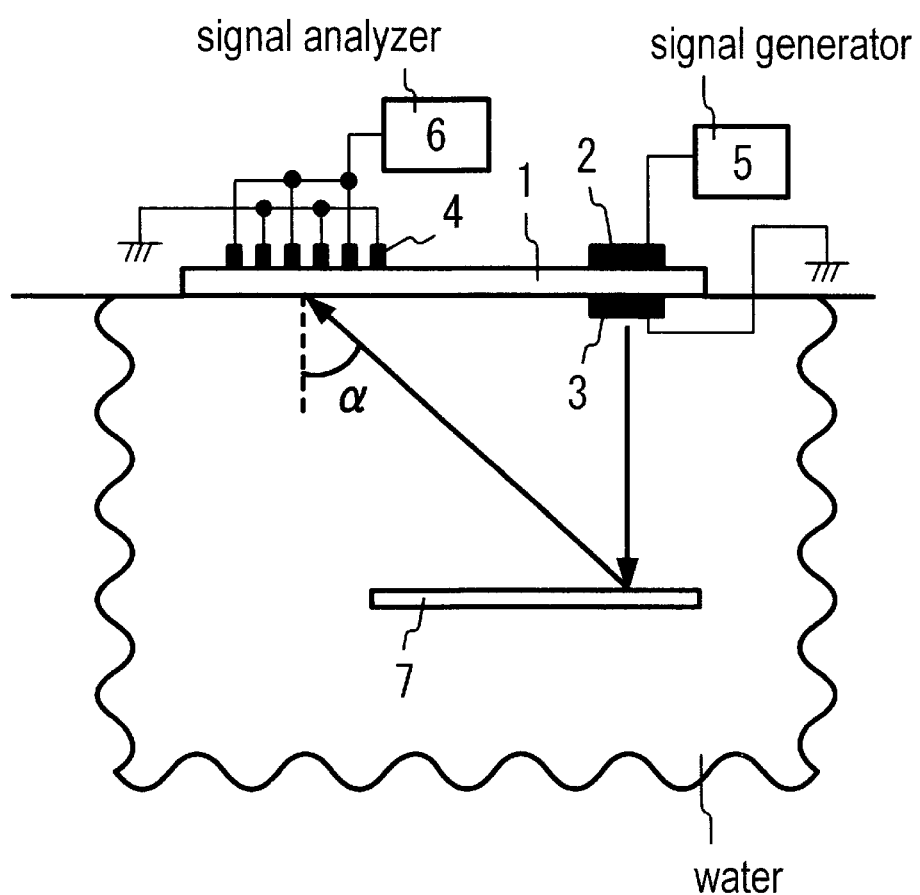
FIG. 3 shows a sectional view of the ultrasonic moving-speed measuring system in FIG. 1.

FIG. 3 shows a sectional view of the ultrasonic moving-speed measuring system in FIG. 1. If an input electric signal with a carrier frequency ($F_0$) is applied from signal generator 5 to the thickness-vibration mode transducer composed of first electrode 2 and second electrode 3, a longitudinal wave is radiated into water along the direction vertical to the lower end surface of piezoelectric substrate 1. In this time, the carrier frequency ($F_0$) is approximately equal to the center frequency for operating the thickness-vibration mode transducer. Thus, the longitudinal wave is effectively radiated into, for example, a cellular tissue, and other medium. If the longitudinal wave is reflected at rotor 7, a delayed electric signal is detected at interdigital transducer 4 via a mode conversion from a reflected longitudinal wave, having a reflection angle (α), to a leaky Lamb wave. The delayed electric signal has a Doppler frequency (F) shifted from the carrier frequency ($F_0$), because of the rotation of rotor 7. In other words, a difference between the carrier- and Doppler frequencies (F–$F_0$) corresponds with a rotating speed (S) of rotor 7. Thus, the rotating speed (S) of rotor 7 is sensed at signal analyzer 6 in terms of the difference between the carrier- and Doppler frequencies (F–$F_0$).

Figure 4:
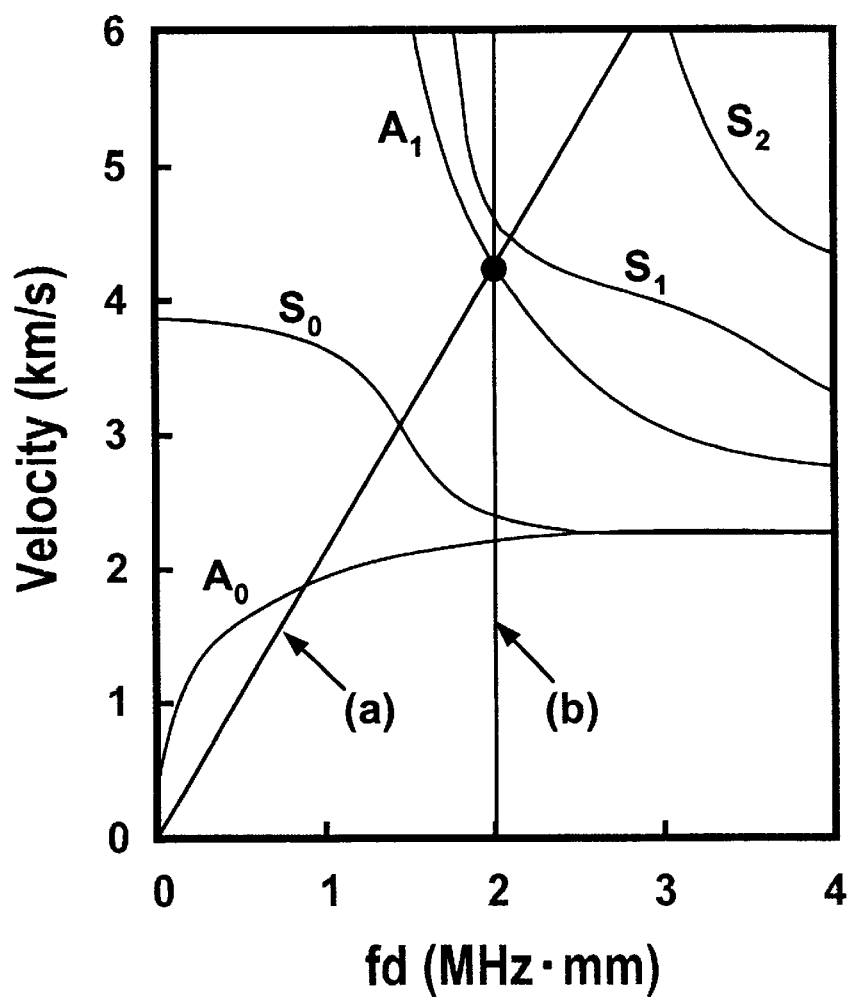
FIG. 4 shows a relationship between the leaky Lamb wave velocity in piezoelectric substrate 1 (V) and the product fd, where f is the frequency and d is the thickness of piezoelectric substrate 1.

FIG. 4 shows a relationship between the leaky Lamb wave velocity in piezoelectric substrate 1 (V) and the product fd, where f is the frequency and d is the thickness of piezoelectric substrate 1. FIG. 4 further shows a line (a) indicating the condition necessary for operation of interdigital transducer 4, and a line (b) indicating the condition necessary for operation of the thickness-vibration mode transducer composed of first electrode 2 and second electrode 3. It is clear that the lines (a) and (b), and the $A_1$ mode curve meet one another at a point ● that corresponds with the most appropriate operation condition, where f=13.13 MHz as d=155 μm, and the leaky Lamb wave velocity in piezoelectric substrate 1 (V) is 4,230 m/s. Thus, it is actually arranged for the ultrasonic moving-speed measuring system in FIG. 1 that both interdigital transducer 4 and the thickness-vibration mode transducer composed of first electrode 2 and second electrode 3 have the same operation frequency as each other. In this time, the reflection angle (α) is 20.51° under a condition that the longitudinal wave velocity in water ($V_W$) is 1,483 m/s at 20° C., because the leaky Lamb wave velocity in piezoelectric substrate 1 (V) is 4,230 m/s.

In FIG. 4, the line (b) shows the condition for operating the thickness-vibration mode transducer at the center frequency. However, it is possible to operate the thickness-vibration mode transducer at a frequency in a frequency band-width of ±6 dB from the center frequency.

Figure 5:
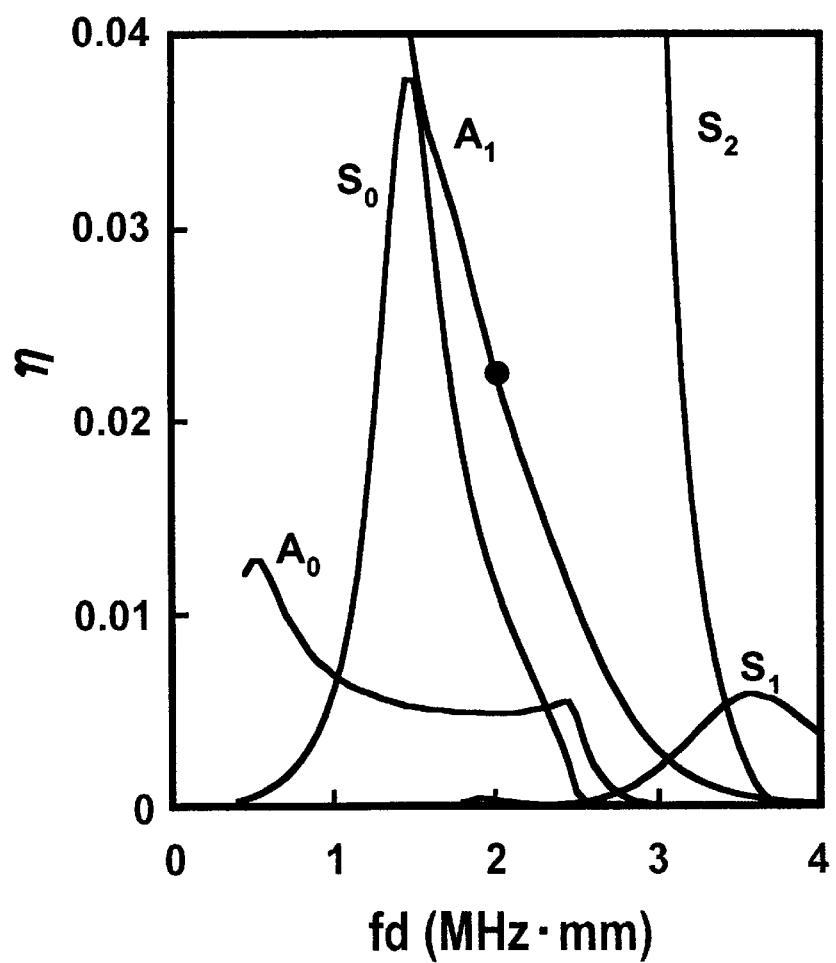
FIG. 5 shows a relationship between the calculated conversion efficiency $\eta$ for a longitudinal wave radiation into a liquid, and the fd value.

FIG. 5 shows a relationship between the calculated conversion efficiency η for a longitudinal wave radiation into a liquid, and the fd value. It should be noticed that a point ● on the $A_1$ mode curve corresponds with the most appropriate operation condition in FIG. 4.

Figure 6:
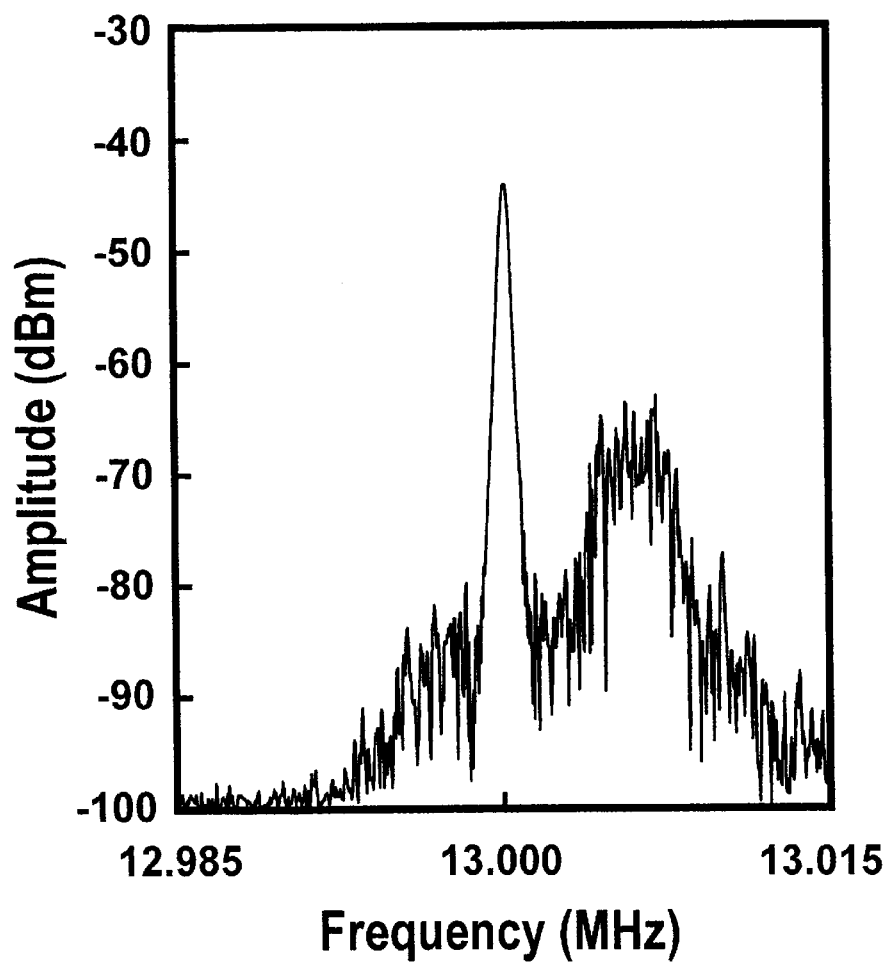
FIG 6 shows an observed spectrum-analysis result at signal analyzer 6 under the condition that the speed of rotor 7 is 1,000 rpm.

FIG. 6 shows an observed spectrum-analysis result at signal analyzer 6 under the condition that the speed of rotor 7 is 1,000 rpm. It should be noticed that the highest peak at 13.13 MHz corresponds with the carrier frequency ($F_0$), and a peak in a higher frequency-band corresponds with the Doppler frequency (F).

Figure 7:
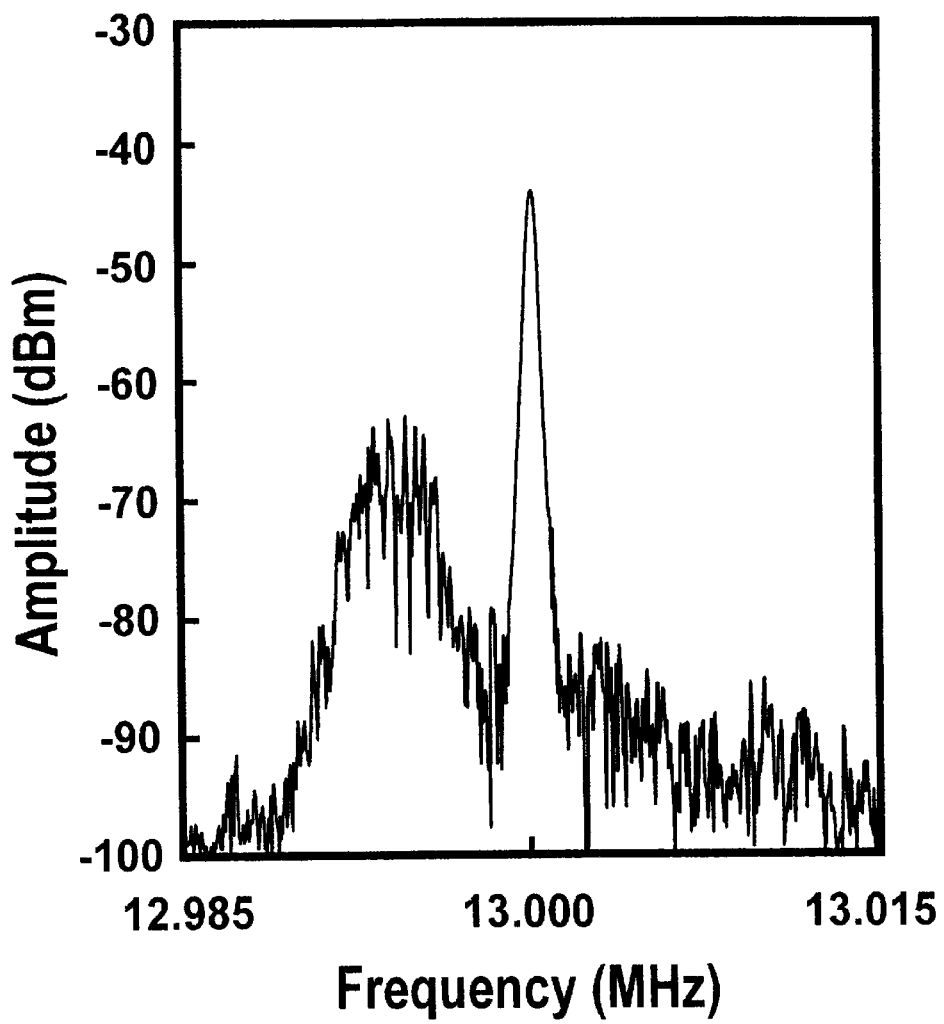
FIG. 7 shows an observed spectrum-analysis result at signal analyzer 6 under the same rotating speed of rotor 7 as FIG. 6, but the reverse rotating direction to the curved arrow in FIG. 1.

FIG. 7 shows an observed spectrum-analysis result at signal analyzer 6 under the same rotating speed of rotor 7 as FIG. 6, but the reverse rotating direction to the curved arrow in FIG. 1.

It should be noticed from FIGS. 6 and 7 that an waveform of a lower frequency-band in FIG. 7 and that of the higher frequency-band in FIG. 6 are approximately symmetrical each other to the carrier frequency ($F_0$) at 13.13 MHz.

Figure 8:
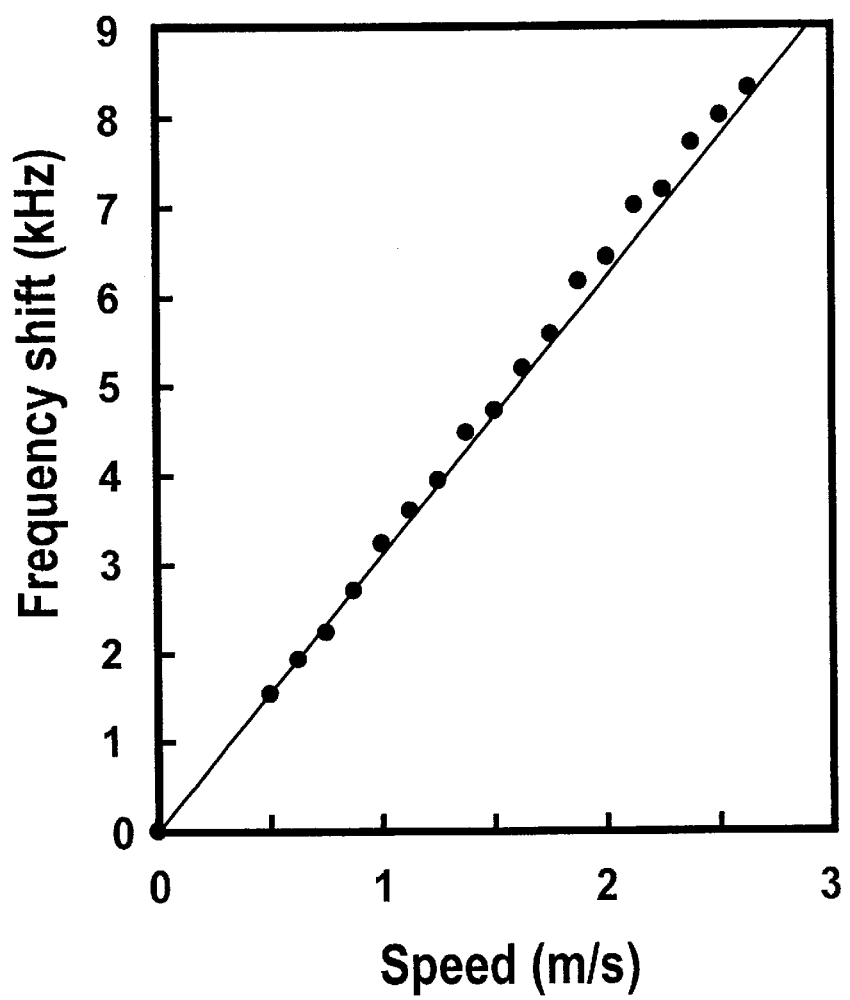
FIG. 8 shows a relationship between the rotating speed (S) of rotor 7 and the difference between the carrier- and Doppler frequencies (F–$F_0$), that is, the frequency shift.

FIG. 8 shows a relationship between the rotating speed (S) of rotor 7 and the difference between the carrier- and Doppler frequencies (F–$F_0$), that is, the frequency shift. It is clear that the observed value indicated by marks ● is approximately coincident with the calculated value indicated by a straight line, and that the frequency shift (F–$F_0$) has a linear relationship with the rotating speed (S), which is calculated according to the following equation:

$$F = F_0 V_W / V_W - S \times \sin \alpha \cos \beta,$$

where F, $F_0$, $V_W$, S, α and β are the Doppler frequency, the carrier frequency, the longitudinal wave velocity in water, the rotating speed (S) of rotor 7, the reflection angle, and an angle made by a reflected longitudinal wave and a rotating direction of rotor 7, respectively. In the case of FIG. 5, α=20.51°, and β=0°.

Figure 9:
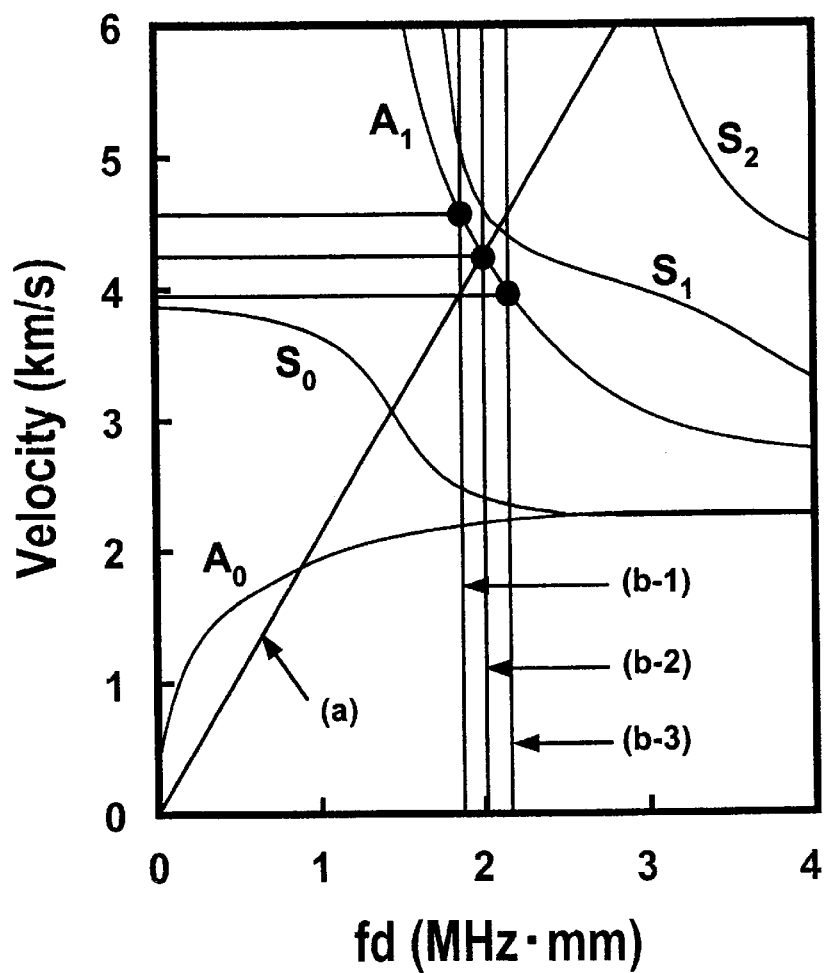
FIG. 9 shows a relationship between the leaky Lamb wave velocity in piezoelectric substrate 1 (V) and the fd value.

FIG. 9 shows a relationship between the leaky Lamb wave velocity in piezoelectric substrate 1 (V) and the fd value. FIG. 9 further shows the line (a) shown in FIG. 4, and three lines (b-1, b-2, and b-3) indicating three different operations of the thickness-vibration mode transducer composed of first electrode 2 and second electrode 3. Each of the three lines (b-1, b-2, and b-3) shows the condition for operating the thickness-vibration mode transducer at a frequency in a frequency band-width of ±6 dB from the center frequency. The line (b-1) and the $A_1$ mode curve meet each other at a point ● that corresponds with a first appropriate operation condition, where f=12 MHz as d=155 μm, and V=4,600 m/s. The line (b-2), the line (a), and the $A_1$ mode curve meet one another at a point ● that corresponds with a second appropriate operation condition, where f=13 MHz as d=155 μm, and V=4,274 m/s. The line (b-3) and the $A_1$ mode curve meet each other at a point ● that corresponds with a third appropriate operation condition, where f=14 MHz as d=155 μm, and V=3,958 m/s.

Figure 10:
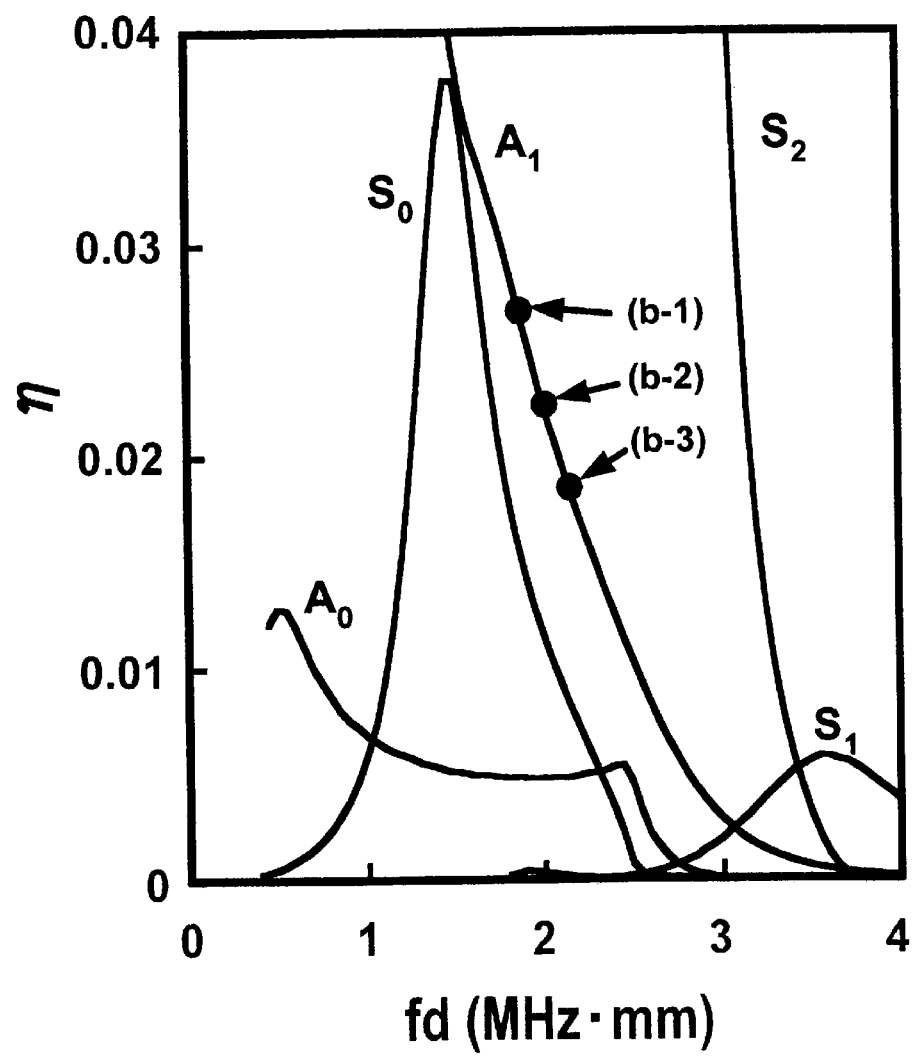
FIG. 10 shows a relationship between the calculated conversion efficiency $\eta$ for a longitudinal wave radiation into a liquid, and the fd value.

FIG. 10 shows a relationship between the calculated conversion efficiency η for a longitudinal wave radiation into a liquid, and the fd value. It should be noticed that three points ● on the $A_1$ mode curve correspond with the first-, second-, and third appropriate operation conditions in FIG. 9, respectively.

Figure 11:
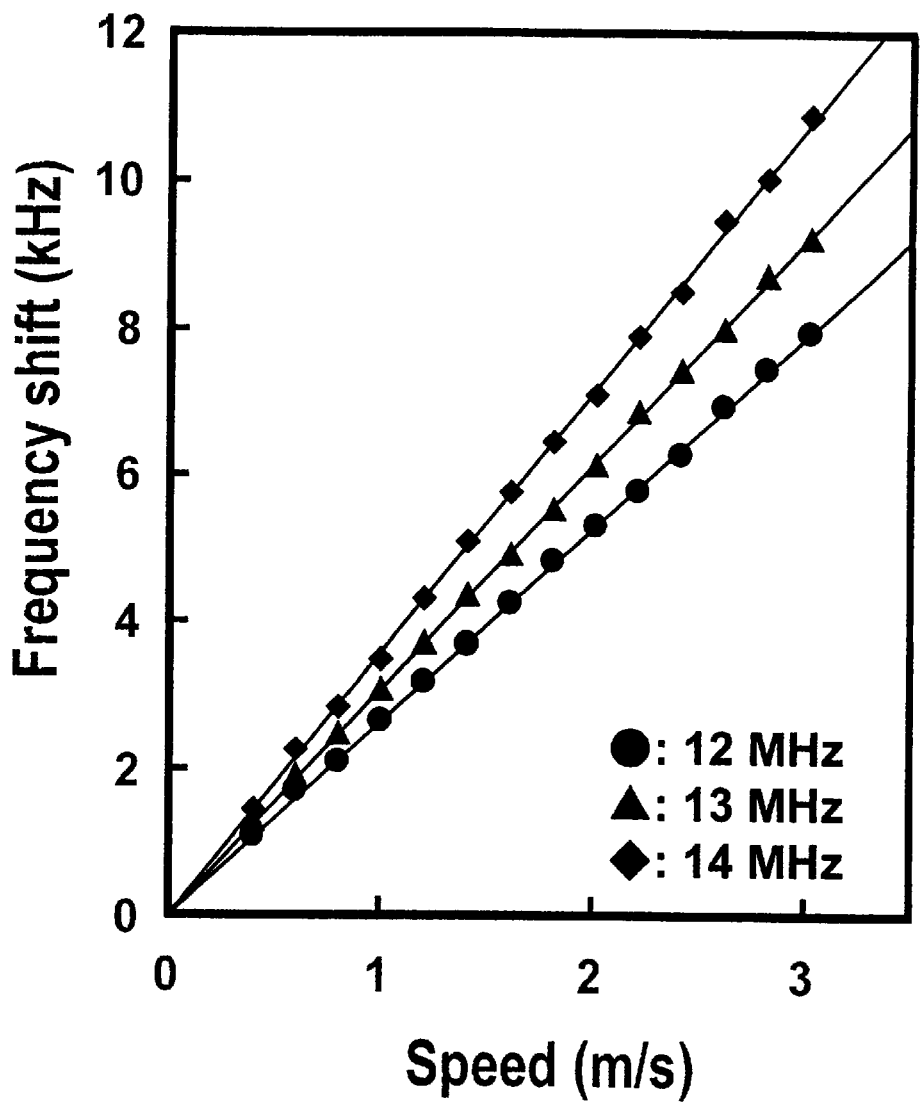
FIG. 11 shows the relationships between the rotating speed (S) of rotor 7, and the frequency shift under three operation conditions of the carrier frequencies (12 MHz, 13 MHz, and 14 MHz).

FIG. 11 shows the relationships between the rotating speed (S) of rotor 7, and the frequency shift under three operation conditions of the carrier frequencies (12 MHz, 13 MHz, and 14 MHz). It is clear that three lines indicating the calculated values, respectively, are approximately coincident with the observed values indicated by a group of marks ●, a group of marks ▲, and a group of marks ◆, respectively. In addition, the frequency shift has a linear relationship with the rotating speed (S). Moreover, it should be noticed from the above equation that the three operation conditions cause three reflection angles ($\alpha_1$, $\alpha_2$ and $\alpha_3$), respectively. In other words, setting a carrier frequency $F_{0i}$ (i=1, 2, . . . , or n) according to a distance $D_i$ (i=1, 2, . . . , or n) between the transducing assembly and rotor 7 in FIG. 1 enables a detection of a reflected longitudinal wave with a reflection angle $\alpha_i$ (i=1, 2, . . . , or n), at interdigital transducer 4, as a delayed electric signal with a Doppler frequency $F_i$ (i=1, 2, . . . , or n).

Figure 12:
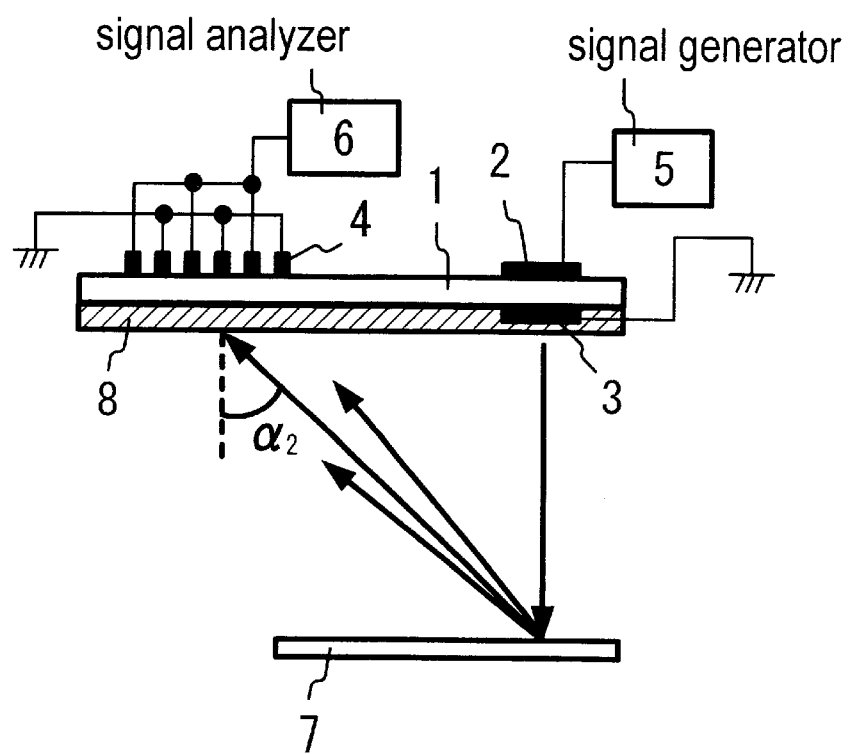
FIG. 12 shows a sectional view of the ultrasonic moving-speed measuring system according to a second embodiment of the present invention.

FIG. 12 shows a sectional view of the ultrasonic moving-speed measuring system according to a second embodiment of the present invention. The ultrasonic moving-speed measuring system has the same construction as FIG. 1, except for the presence of nonpiezoelectric film 8 made of silicone rubber. The bottom of the transducing assembly is covered with nonpiezoelectric film 8.

In the ultrasonic moving-speed measuring system in FIG. 12, when an input electric signal ($E_1$, $E_2$ or $E_3$) with a carrier frequency ($F_{01}$, $F_{02}$ or $F_{03}$), respectively, is applied from signal generator 5 to the thickness-vibration mode transducer composed of first electrode 2 and second electrode 3, a longitudinal wave along the direction vertical to the lower end surface of piezoelectric substrate 1 is radiated into water. The use of nonpiezoelectric film 8 such as silicone rubber makes it possible to radiate the longitudinal wave into water with high efficiency. When the longitudinal wave is reflected at rotor 7, a reflected longitudinal wave has a reflection angle ($\alpha_1$, $\alpha_2$ or $\alpha_3$) in response to the carrier frequency ($F_{01}$, $F_{02}$ or $F_{03}$), respectively. In FIG. 12, a delayed electric signal with a Doppler frequency ($F_2$) is detected at interdigital transducer 4 via a mode conversion from the reflected longitudinal wave with the reflection angle ($\alpha_2$) to a leaky Lamb wave. In other words, setting the carrier frequency ($F_{01}$, $F_{02}$ or $F_{03}$) according to a distance ($D_1$, $D_2$ or $D_3$), respectively, between the transducing assembly and rotor 7 makes interdigital transducer 4 detect the delayed electric signal with the Doppler frequency ($F_1$, $F_2$ or $F_3$) via the mode conversion from the reflected longitudinal wave with the reflection angle ($\alpha_1$, $\alpha_2$ or $\alpha_3$) to the leaky Lamb wave. In this time, the use of nonpiezoelectric film 8 causes the mode conversion from the reflected longitudinal wave to the leaky Lamb wave with high efficiency.

Figure 13:
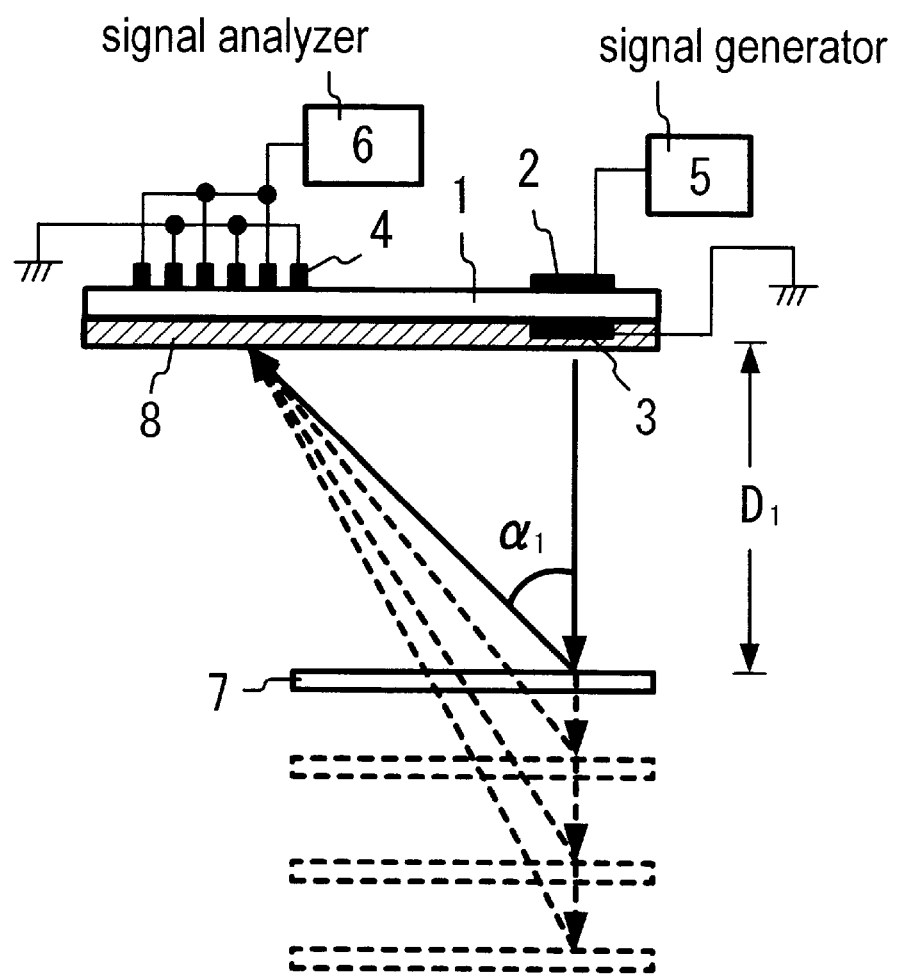
FIG. 13 shows another sectional view of the ultrasonic moving-speed measuring system in FIG. 12, in case that rotor 7 stays at four positions, respectively, in water.

FIG. 13 shows another sectional view of the ultrasonic moving-speed measuring system in FIG. 12, in case that rotor 7 stays at four positions, respectively, in water. It should be noticed that setting a carrier frequency $F_{0i}$ (i=1, 2, 3 or 4) according to a distance $D_i$ (i=1, 2, 3 or 4) between the transducing assembly and rotor 7 makes interdigital transducer 4 detect a delayed electric signal with a Doppler frequency $F_i$ (i=1, 2, 3 or 4) via a mode conversion from a reflected longitudinal wave with a reflection angle $\alpha_i$ (i=1, 2, 3 or 4) to a leaky Lamb wave. In this time, the higher carrier frequency, the larger reflection angle.

Figure 14:
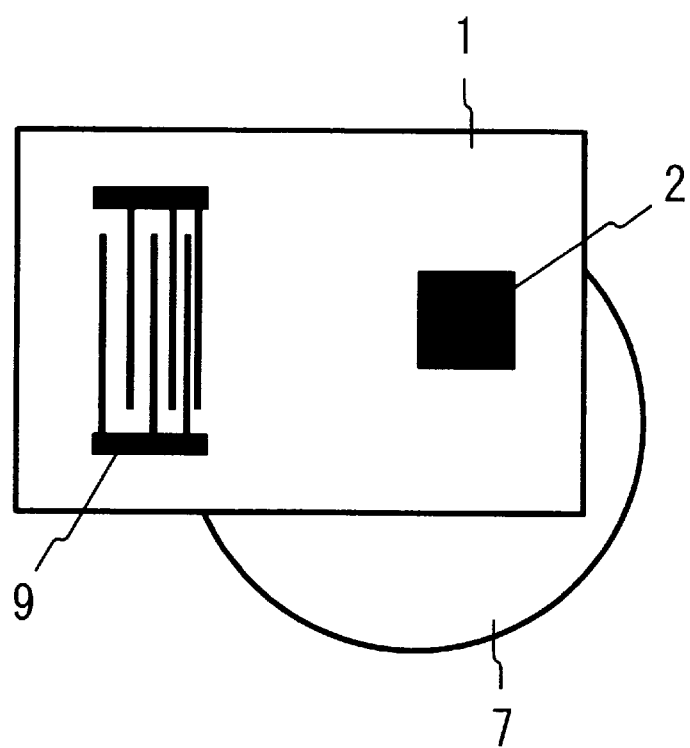
FIG. 14 shows a top plan view of an ultrasonic moving-speed measuring system according to a third embodiment of the present invention.

FIG. 14 shows a top plan view of an ultrasonic moving-speed measuring system according to a third embodiment of the present invention. The ultrasonic moving-speed measuring system has the same construction as FIG. 1, except for the presence of interdigital transducer 9 in place of interdigital transducer 4. Interdigital transducer 9 has the same number of electrode-finger pairs and the same finger-overlap length (L) as interdigital transducer 4, however, has a dispersive electrode-pattern different from a normal electrode-pattern in interdigital transducer 4. Thus, interdigital transducer 9 has interdigital periodicities of 283~383 $\mu$m. In addition, the smaller interdigital periodicity, the nearer first electrode 2. When sensing a rotating speed (S) of rotor 7 in water, the bottom of the transducing assembly is kept in contact with water.

In the ultrasonic moving-speed measuring system in FIG. 14, when an input electric signal with a carrier frequency ($F_0$) is applied to the thickness-vibration mode transducer composed of first electrode 2 and second electrode 3, a longitudinal wave is radiated into water. And then, if the longitudinal wave is reflected at rotor 7, a delayed electric signal with a Doppler frequency (F) is detected at interdigital transducer 9 via a mode conversion from a reflected longitudinal wave, having a reflection angle ($\alpha$), to a leaky Lamb wave. As mentioned above, a difference between the carrier- and Doppler frequencies ($F-F_0$) corresponds with the rotating speed (S) of rotor 7. In other words, the higher speed (S) of rotor 7, the higher Doppler frequency (F), or the lower Doppler frequency (F) in case of the reverse rotation of rotor 7. A higher speed (S) of rotor 7 causes a reflected longitudinal wave with a shorter wavelength, so that a delayed electric signal with a higher Doppler frequency (F) is detected at a finger-part, with a smaller interdigital periodicity, of interdigital transducer 9. In case of the reverse rotation of rotor 7, a higher speed (S) of rotor 7 causes a reflected longitudinal wave with a longer wavelength, so that a delayed electric signal with a lower Doppler frequency (F) is detected at a finger-part, with a larger interdigital periodicity, of interdigital transducer 9. Accordingly, interdigital transducer 9 with the dispersive electrode-pattern is of much avail for various-speed rotation of rotor 7.

Figure 15:
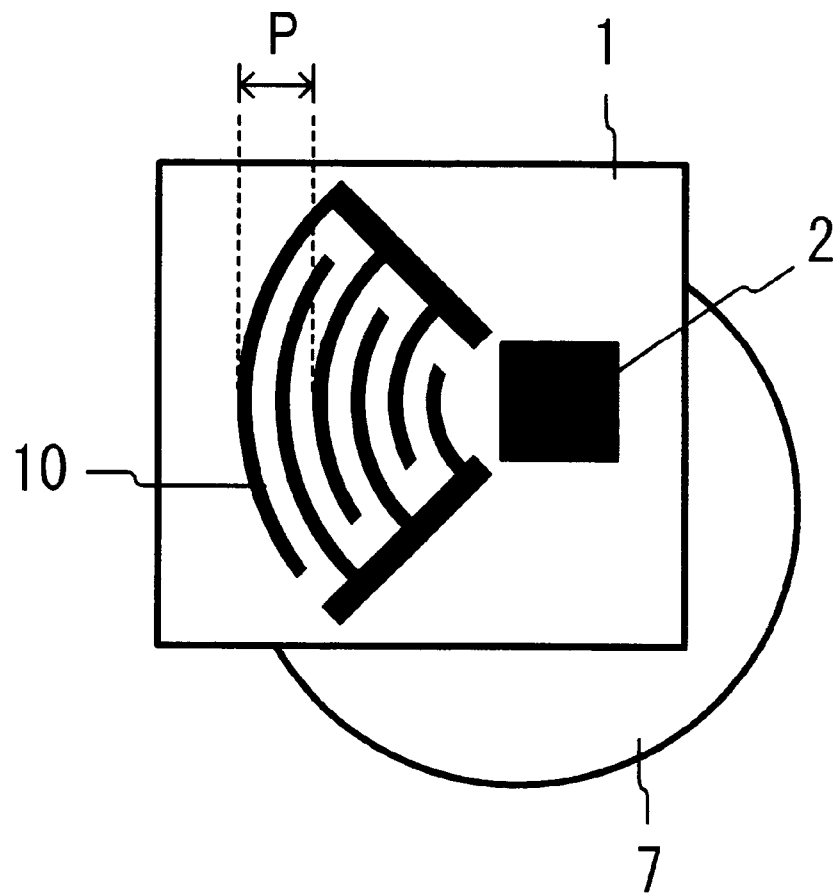
FIG. 15 shows a top plan view of an ultrasonic moving-speed measuring system according to a fourth embodiment of the present invention.

FIG. 15 shows a top plan view of an ultrasonic moving-speed measuring system according to a fourth embodiment of the present invention. The ultrasonic moving-speed measuring system has the same construction as FIG. 1, except for the presence of interdigital transducer 10 in place of interdigital transducer 4. Interdigital transducer 10 has an arch-shaped electrode-pattern with a concentric center at a coincident situation with the center of first electrode 2, and has ten electrode-finger pairs, an interdigital periodicity (P) of 320 $\mu$m, and an aperture angle of 45°. The use of the ultrasonic moving-speed measuring system in FIG. 15 makes the same sensing ability as that in FIG. 1.

Figure 16:
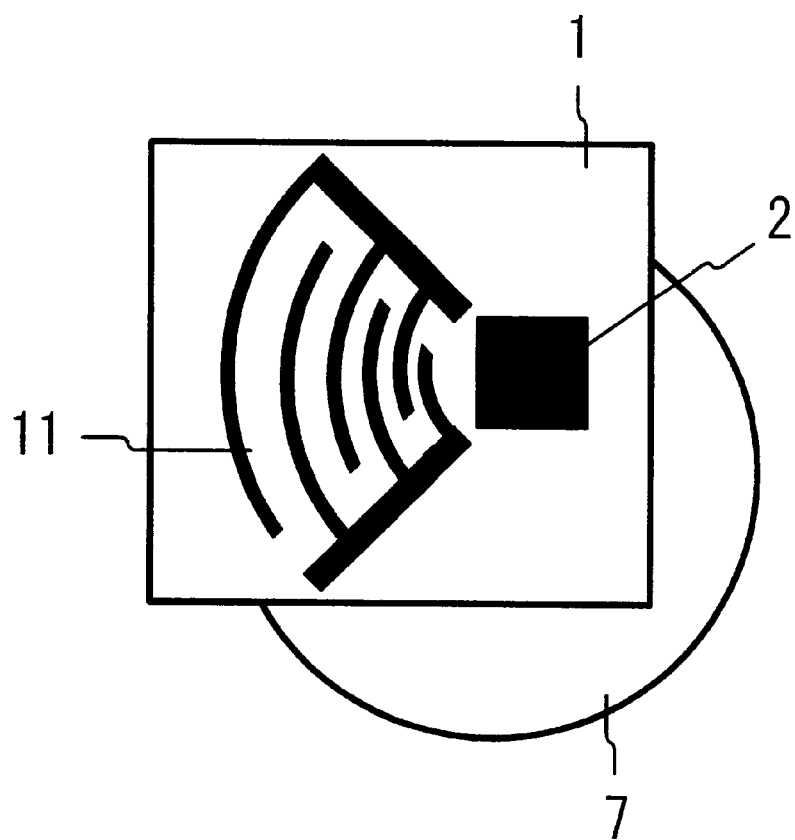
FIG. 16 shows a top plan view of an ultrasonic moving-speed measuring system according to a fifth embodiment of the present invention.

FIG. 16 shows a top plan view of an ultrasonic moving-speed measuring system according to a fifth embodiment of the present invention. The ultrasonic moving-speed measuring system has the same construction as FIG. 15, except for the presence of interdigital transducer 11 in place of interdigital transducer 10. Interdigital transducer 11 has the same arch-shaped electrode-pattern, the same number of electrode-finger pairs, and the same aperture angle as interdigital transducer 10, however, has a dispersive electrode-pattern different from a normal electrode-pattern in interdigital transducer 10. Thus, interdigital transducer 11 has interdigital periodicities of 283~383 $\mu$m. In addition, the smaller interdigital periodicity, the nearer first electrode 2. In the same way as FIG. 14, interdigital transducer 11 is available for a various-speed rotation of rotor 7 in comparison with interdigital transducer 10.

Figure 17:
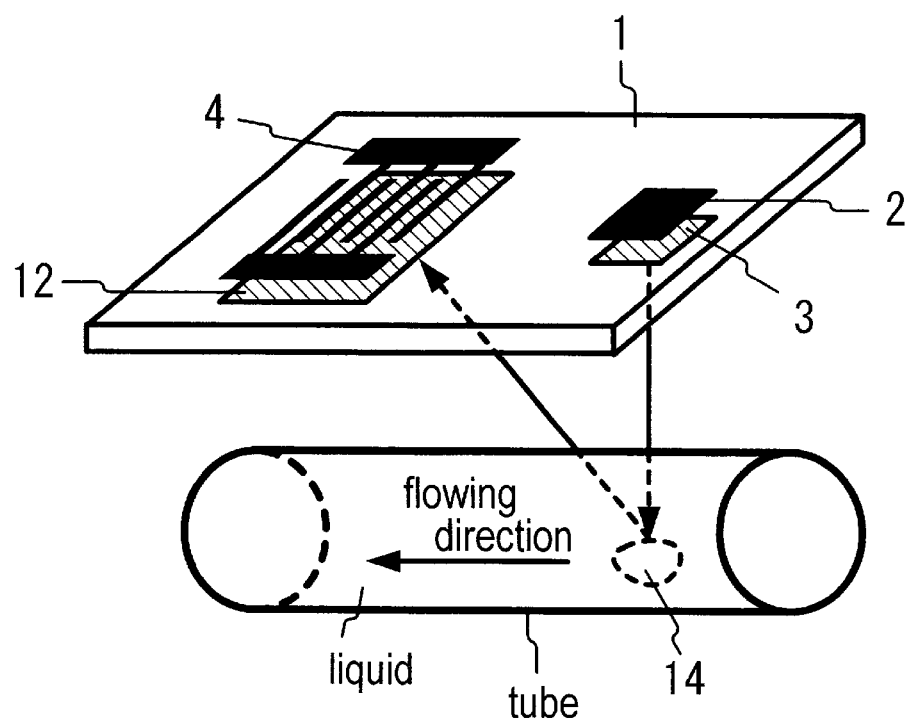
FIG. 17 shows a schematic illustration of an ultrasonic moving-speed measuring system according to a sixth embodiment of the present invention.

FIG. 17 shows a schematic illustration of an ultrasonic moving-speed measuring system according to a sixth embodiment of the present invention. The ultrasonic moving-speed measuring system has the same construction as FIG. 1, except for the presence of counter electrode 12 and amplifier 13 that is not drawn in FIG. 17, and the absence of signal generator 5. Counter electrode 12, with a rectangular plate-shape and made of an aluminum thin film, is formed on the lower end surface of piezoelectric substrate 1 and located at the corresponding position with interdigital transducer 4. Thus, piezoelectric substrate 1, the thickness-vibration mode transducer, interdigital transducer 4, and counter electrode 12 form a transducing assembly. When sensing, for example, a flowing speed (S) of a liquid in a tube that exists in a medium, the bottom of the transducing assembly is kept in contact with the medium. In this time, material 14 in the liquid is flowing in accordance with the flowing speed (S) and flowing direction of the liquid.

Figure 18:
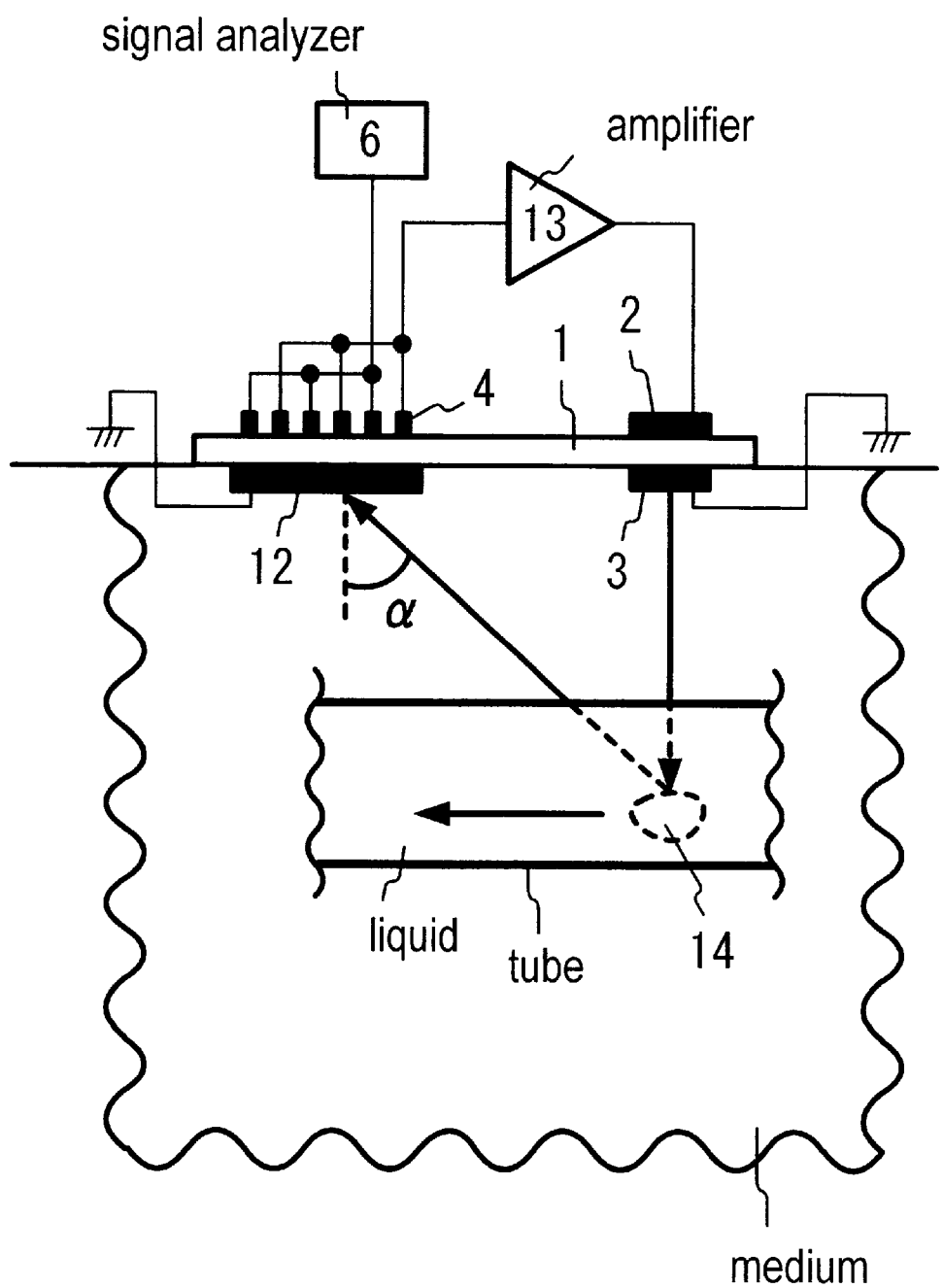
FIG. 18 shows a sectional view of the ultrasonic moving-speed measuring system in FIG. 17.

FIG. 18 shows a sectional view of the ultrasonic moving-speed measuring system in FIG. 17. When an input electric signal with a carrier frequency ($F_O$) is applied to the thickness-vibration mode transducer composed of first electrode 2 and second electrode 3, a longitudinal wave is radiated into the medium, and then, into the liquid through the tube. If the longitudinal wave is reflected at material 14, a delayed electric signal with a Doppler frequency (F) is detected between interdigital transducer 4 and counter electrode 12 via a mode conversion from a reflected longitudinal wave, having a reflection angle ($\alpha$), to a leaky Lamb wave. The flowing speed (S) of the liquid is sensed at signal analyzer 6 in terms of the difference between the carrier- and Doppler frequencies ($F-F_O$), because material 14 is flowing in accordance with the flowing speed (S) and flowing direction of the liquid. Thus, when the medium, the tube, the liquid, and material 14 correspond with, for example, a cellular tissue, a blood vessel, blood, and blood cell, respectively, the flowing speed (S) of blood is evaluated effectively. The delayed electric signal is not only detected at signal analyzer 6, but also amplified via amplifier 13. The amplified electric signal is applied to the thickness-vibration mode transducer composed of first electrode 2 and second electrode 3 again. Supplying the thickness-vibration mode transducer with the amplified electric signal causes a self-oscillation, and moreover causes the circuit construction simplified.

In the ultrasonic moving-speed measuring system in FIGS. 12, 14, 15 and 16, it is possible to use a counter electrode, which is formed on the lower end surface of piezoelectric substrate 1, and is located at the corresponding position with interdigital transducers 4, 9, 10 and 11, respectively.

Figure 19:
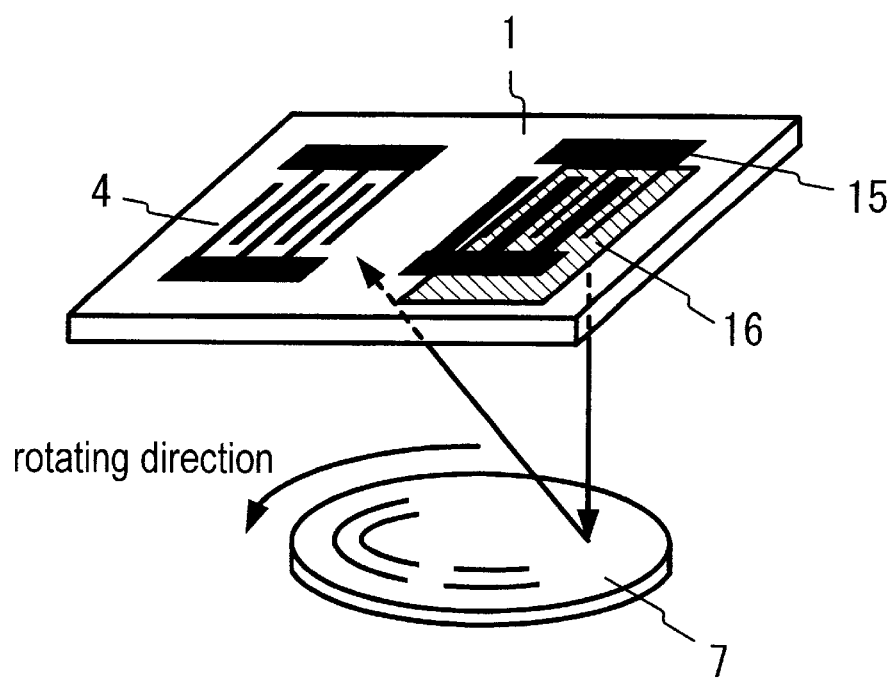
FIG. 19 shows a schematic illustration of an ultrasonic moving-speed measuring system according to a seventh embodiment of the present invention.

FIG. 19 shows a schematic illustration of an ultrasonic moving-speed measuring system according to a seventh embodiment of the present invention. The ultrasonic moving-speed measuring system has the same construction as FIG. 1, except for the presence of interdigital arrangement 15 and second electrode 16, in place of first electrode 2 and second electrode 3, respectively. Thus, piezoelectric substrate 1, interdigital arrangement 15, second electrode 16, and interdigital transducer 4 form a transducing assembly. When sensing a rotating speed (S) of rotor 7 in water, the bottom of the transducing assembly is kept in contact with water.

Figure 20:
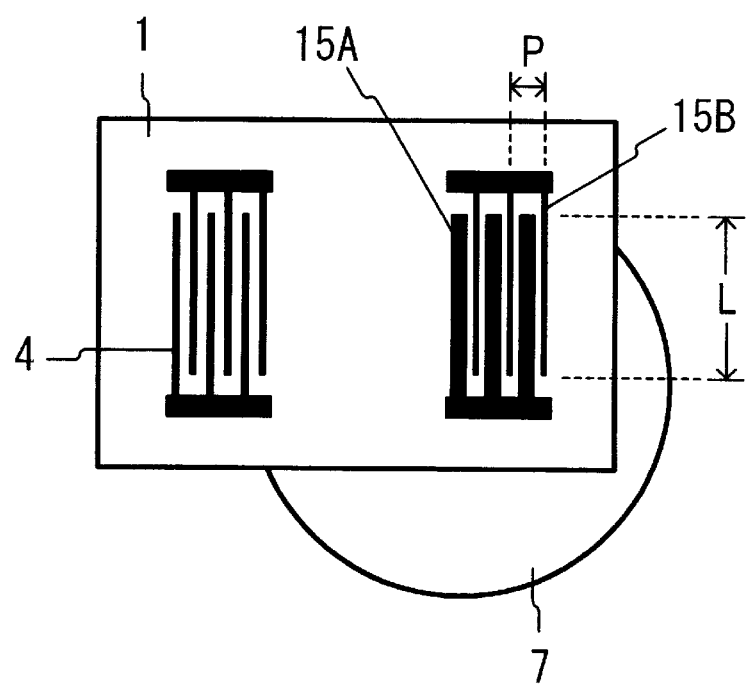
FIG. 20 shows a top plan view of the transducing assembly in FIG. 19 and rotor 7.

FIG. 20 shows a top plan view of the transducing assembly in FIG. 19 and rotor 7. Second electrode 16 is not drawn in FIG. 20. Interdigital arrangement 15 is composed of two comb-shaped electrodes (15A and 15B), and has the same number of electrode-finger pairs, the same finger-overlap length (L), and the same interdigital periodicity (P) as interdigital transducer 4. However, comb-shaped electrode 15A has a finger width ($W_A$) of 64 $\mu$m, and comb-shaped electrode 15B has a finger width ($W_B$) of 16 $\mu$m.

In the ultrasonic moving-speed measuring system in FIG. 19, when an input electric signal with a carrier frequency ($F_O$) is applied to a thickness-vibration mode transducer composed of comb-shaped electrode 15A and second electrode 16, a longitudinal wave is radiated into water. As mentioned above, the longitudinal wave velocity in water ($V_W$) is 1,483 m/s at 20° C., and the leaky Lamb wave velocity in piezoelectric substrate 1 (V) is 4,230 m/s. Thus, the ratio of ($V_W$) to (V), that is 1,483/4,230, is approximately 0.35. On the other hand, the ratio of the interdigital periodicity (P) of interdigital arrangement 15 to the thickness (d) of piezoelectric substrate 1, that is 320/155, is approximately 2, which is larger than five times the ratio of the ($V_W$) to (V). Such a condition of $P/d \geqq 5V_W/V$ enables a multidirectional radiation into water, that is, makes the longitudinal wave composed of the main lobe and the grating lobes effectively radiated into water. In this time, the main lobe and the grating lobes corresponds with the vertical- and slant components, respectively, to the lower end surface of piezoelectric substrate 1. The condition that comb-shaped electrode 15B is electrically floated or grounded has influence upon the intensity of the grating lobes. The condition that comb-shaped electrode 15B is electrically floated makes the grating lobes smaller. Moreover, the condition that the finger width of comb-shaped electrode 15A is larger than that of comb-shaped electrode 15B makes the grating lobes smaller. Thus, it is easy to radiate the main lobe, that is, a longitudinal wave vertical to the lower end surface of piezoelectric substrate 1, into water by interdigital arrangement 15. On the other hand, it is easy to detect a reflected longitudinal wave slant to the lower end surface of piezoelectric substrate 1 by interdigital transducer 4. Thus, when the main lobe of the longitudinal wave is reflected at rotor 7, a delayed electric signal with a Doppler frequency (F) is detected via a mode conversion from a reflected longitudinal wave, having a reflection angle ($\alpha$), to a leaky Lamb wave at interdigital transducer 4. As a result, the rotating speed (S) of rotor 7 is sensed at signal analyzer 6 in terms of the difference between the carrier- and Doppler frequencies ($F-F_O$).

In the ultrasonic moving-speed measuring system in FIG. 19, it is possible to use a counter electrode, which is formed on the lower end surface of piezoelectric substrate 1, and is located at the corresponding position with interdigital transducer 4.

Figure 21:
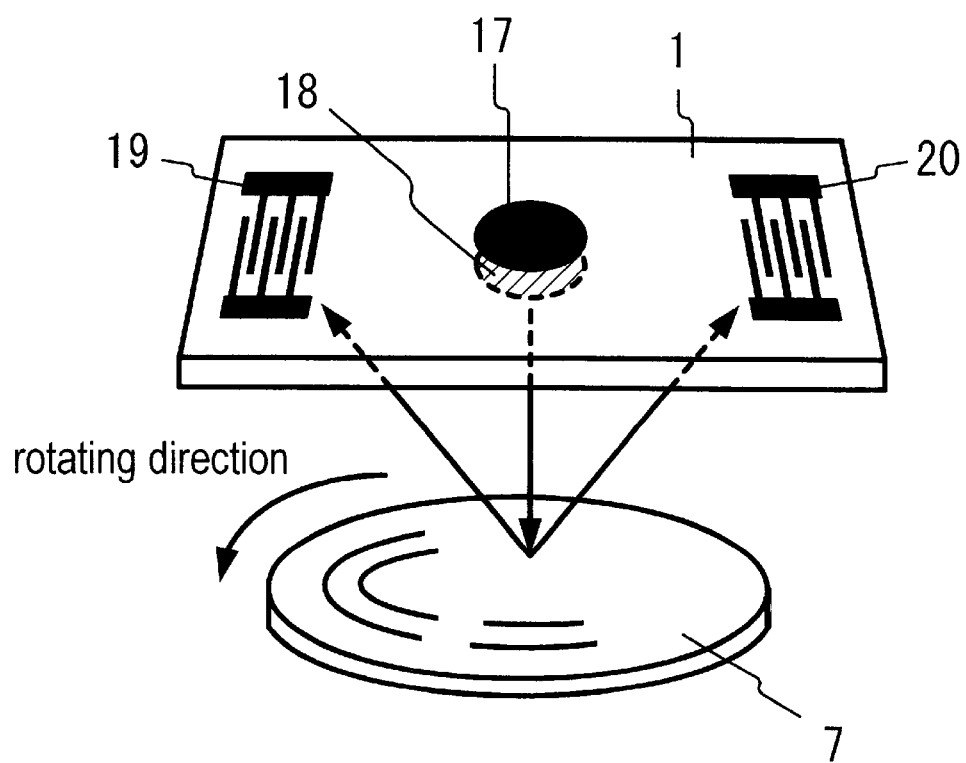
FIG. 21 shows a schematic illustration of an ultrasonic moving-speed measuring system according to an eighth embodiment of the present invention.

FIG. 21 shows a schematic illustration of an ultrasonic moving-speed measuring system according to an eighth embodiment of the present invention. The ultrasonic moving-speed measuring system comprises piezoelectric substrate 1, first electrode 17, second electrode 18, first interdigital transducer 19, and second interdigital transducer 20, and then, further comprises signal generator 5, and signal analyzer 6, which are not drawn in FIG. 21. Thus, the ultrasonic moving-speed measuring system in FIG. 21 has the same construction as FIG. 1, except for the absence of interdigital transducer 4, the presence of first interdigital transducer 19 and second interdigital transducer 20, and the presence of first electrode 17 and second electrode 18 in place of first electrode 2 and second electrode 3, respectively. First electrode 17 and second electrode 18 have a disk-shape, respectively, and they together form a thickness-vibration mode transducer. First interdigital transducer 19 and second interdigital transducer 20 have the same electrode patterns as interdigital transducer 4. First electrode 17 is located between first interdigital transducer 19 and second interdigital transducer 20. In this way, piezoelectric substrate 1, the thickness-vibration mode transducer, first interdigital transducer 19, and second interdigital transducer 20 form a transducing assembly. When sensing a rotating speed (S) of rotor 7 in water, the bottom of the transducing assembly is kept in contact with water.

Figure 22:
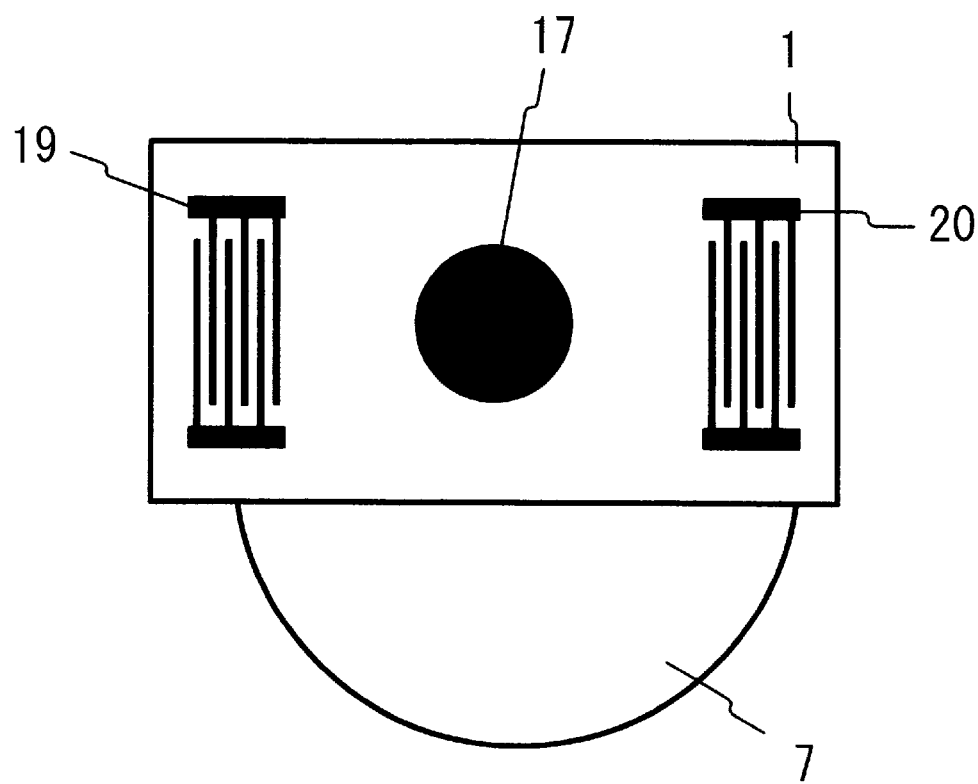
FIG. 22 shows a top plan view of the transducing assembly in FIG. 21 and rotor 7.

FIG. 22 shows a top plan view of the transducing assembly in FIG. 21 and rotor 7. Second electrode 18 is not drawn in FIG. 22. It should be noted that an intersecting line on each finger-center of the finger overlap-zone of first interdigital transducer 19 and that of second interdigital transducer 20 overlap each other. When an input electric signal with a carrier frequency ($F_0$) is applied to the thickness-vibration mode transducer composed of first electrode 17 and second electrode 18, a longitudinal wave is radiated into water. If the longitudinal wave is reflected at rotor 7, a first delayed electric signal with a first Doppler frequency ($F_f$) is detected at first interdigital transducer 19 via a mode conversion from a first reflected longitudinal wave having a reflection angle ($\alpha$) to a first leaky Lamb wave, and at the same time, a second delayed electric signal with a second Doppler frequency ($F_s$) is detected at second interdigital transducer 20 via a mode conversion from a second reflected longitudinal wave having the reflection angle ($\alpha$) to a second leaky Lamb wave. In this time, the first Doppler frequency ($F_f$) is larger than the carrier frequency ($F_0$), and the second Doppler frequency ($F_s$) is smaller than the carrier frequency ($F_0$), because of the rotating direction of rotor 7. In other words, detecting a larger Doppler frequency decides the rotating direction. As a result, the rotating direction and the rotating speed (S) of rotor 7 is sensed at signal analyzer 6 in terms of a difference between the carrier frequency ($F_0$) and a larger one of the first- and second Doppler frequencies ($F_f$ and $F_s$). In addition, the use of two equivalent interdigital transducers, that is, first interdigital transducer 19 and second interdigital transducer 20, cancels a change in circumstances such as temperature, pressure, and so on.

In the ultrasonic moving-speed measuring system in FIG. 21, the use of two interdigital transducers 9 shown in FIG. 14, in place of first interdigital transducer 19 and second interdigital transducer 20, causes availability for various-speed rotation of rotor 7.

Figure 23:
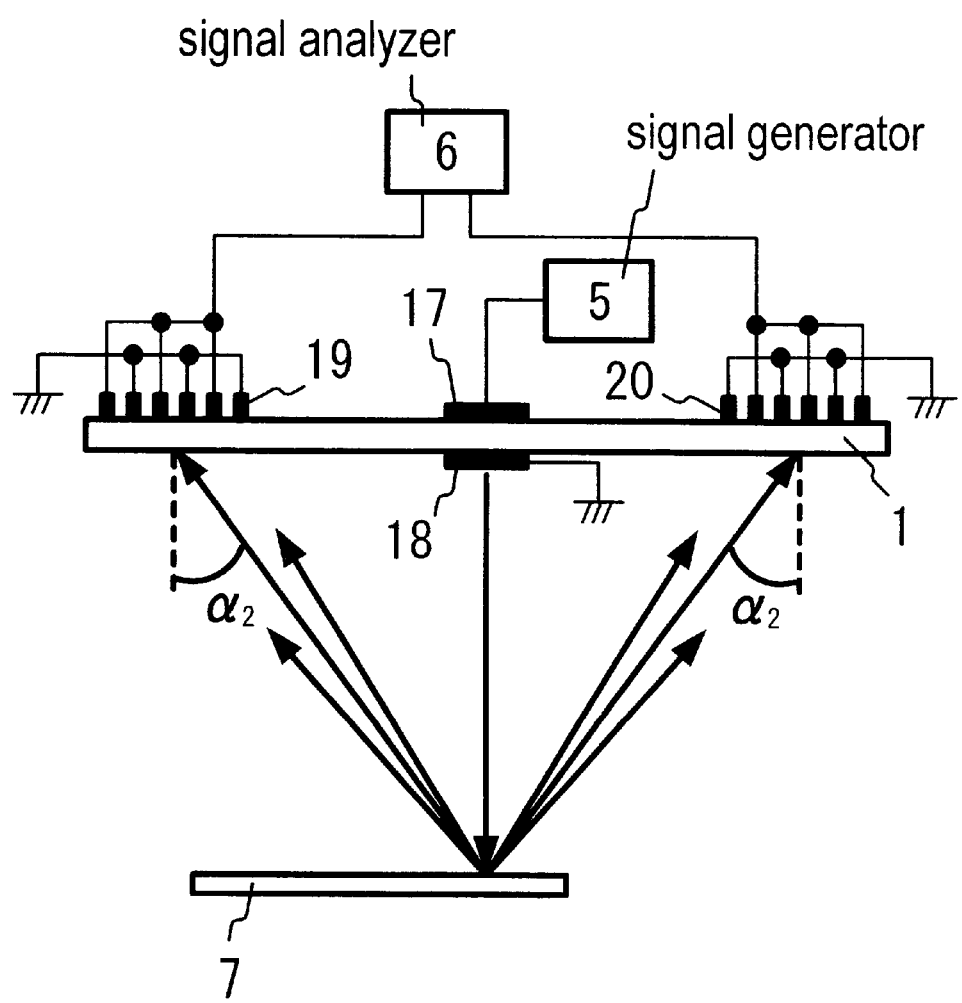
FIG. 23 shows a sectional view of the ultrasonic moving-speed measuring system in FIG. 21.

FIG. 23 shows a sectional view of the ultrasonic moving-speed measuring system in FIG. 21. If an input electric signal ($E_1$, $E_2$ or $E_3$) with a carrier frequency ($F_{01}$, $F_{02}$ or $F_{03}$), respectively, is applied to the thickness-vibration mode transducer composed of first electrode 17 and second electrode 18, a longitudinal wave is radiated into water. When the longitudinal wave is reflected at rotor 7, a first delayed electric signal with a first Doppler frequency ($F_{f1}$, $F_{f2}$ or $F_{f3}$) is detected at first interdigital transducer 19 via a mode conversion from a first reflected longitudinal wave to a first leaky Lamb wave. The first reflected longitudinal wave has a reflection angle ($\alpha_1$, $\alpha_2$ or $\alpha_3$) in response to the carrier frequency ($F_{01}$, $F_{02}$ or $F_{03}$), respectively. At the same time, a second delayed electric signal with a second Doppler frequency ($F_{s1}$, $F_{s2}$ or $F_{s3}$) is detected at second interdigital transducer 20 via a mode conversion from a second reflected longitudinal wave having the reflection angle ($\alpha_1$, $\alpha_2$ or $\alpha_3$) to a second leaky Lamb wave. In FIG. 23, a first delayed electric signal with a first Doppler frequency ($F_{f2}$) is effectively detected at first interdigital transducer 19 via a mode conversion from the first reflected longitudinal wave with the reflection angle ($\alpha_2$) to a first leaky Lamb wave, and a second delayed electric signal with a second Doppler frequency ($F_{s2}$) is effectively detected at second interdigital transducer 20 via a mode conversion from the second reflected longitudinal wave with the reflection angle ($\alpha_2$) to a second leaky Lamb wave. Thus, setting the carrier frequency ($F_{01}$, $F_{02}$ or $F_{03}$) according to a distance ($D_1$, $D_2$ or $D_3$) between the transducing assembly and rotor 7 makes first interdigital transducer 19 detect the first delayed electric signal with the first Doppler frequency ($F_{f1}$, $F_{f2}$ or $F_{f3}$) via the mode conversion from the first reflected longitudinal wave with the reflection angle ($\alpha_1$, $\alpha_2$ or $\alpha_3$) to the first leaky Lamb wave, and second interdigital transducer 20 detect the second delayed electric signal with the second Doppler frequency ($F_{s1}$, $F_{s2}$ or $F_{s3}$) via the mode conversion from the second reflected longitudinal wave with the reflection angle ($\alpha_1$, $\alpha_2$ or $\alpha_3$) to the second leaky Lamb wave.

Figure 24:
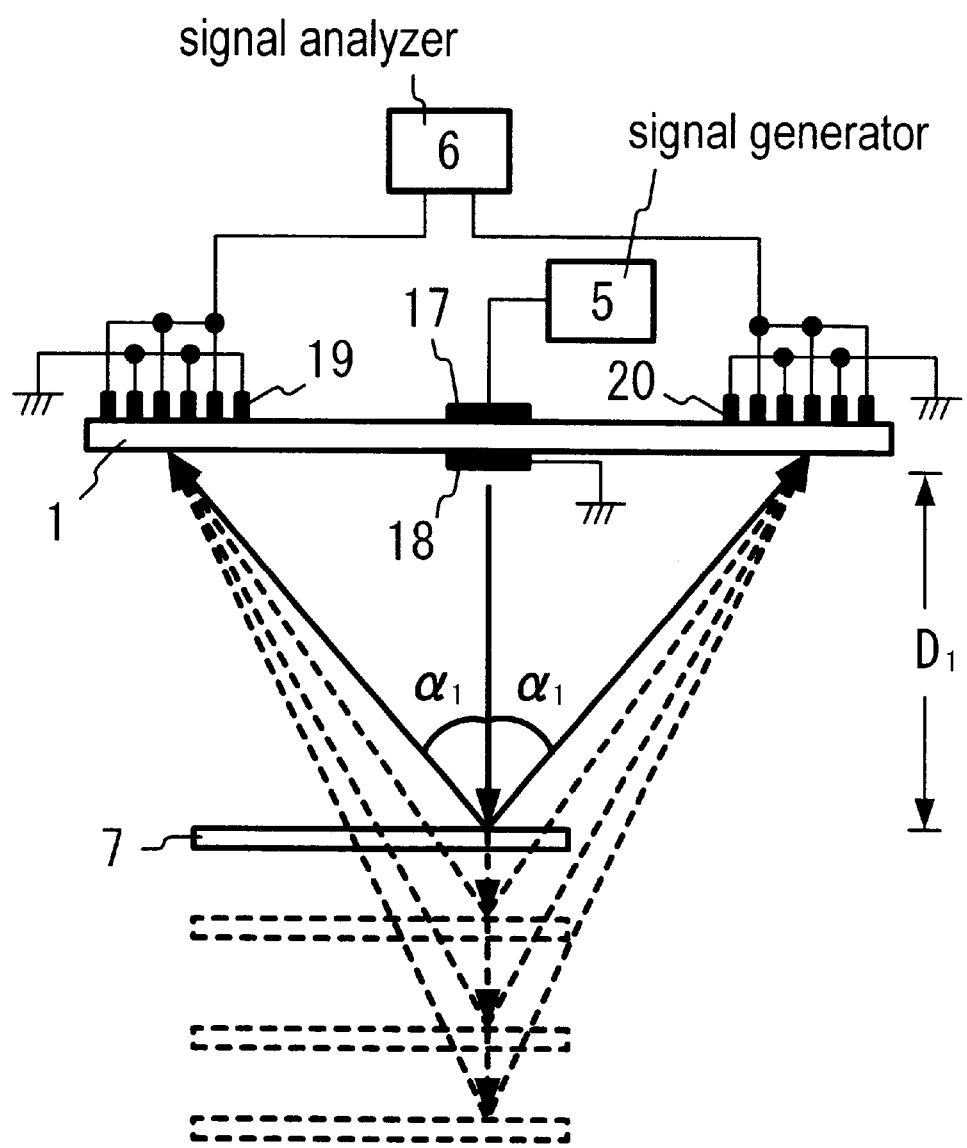
FIG. 24 shows another sectional view of the ultrasonic moving-speed measuring system in FIG. 21, in case that rotor 7 stays at four positions, respectively, in water.

FIG. 24 shows another sectional view of the ultrasonic moving-speed measuring system in FIG. 21, in case that rotor 7 stays at four positions, respectively, in water. It should be noticed that setting a carrier frequency $F_{0i}$ (i=1, 2, 3 or 4) according to a distance $D_i$ (i=1, 2, 3 or 4) between the transducing assembly and rotor 7 makes first interdigital transducer 19 detect the first delayed electric signal with the first Doppler frequency $F_{fi}$ (i=1, 2, 3 or 4) via the mode conversion from the first reflected longitudinal wave with the reflection angle $\alpha_i$ (i=1, 2, 3 or 4) to the first leaky Lamb wave, and second interdigital transducer 20 detect the second delayed electric signal with the second Doppler frequency $F_{si}$ (i=1, 2, 3 or 4) via the mode conversion from the second reflected longitudinal wave with the reflection angle $\alpha_i$ (i=1, 2, 3 or 4) to the second leaky Lamb wave. In this time, the higher carrier frequency, the larger reflection angle.

Figure 25:
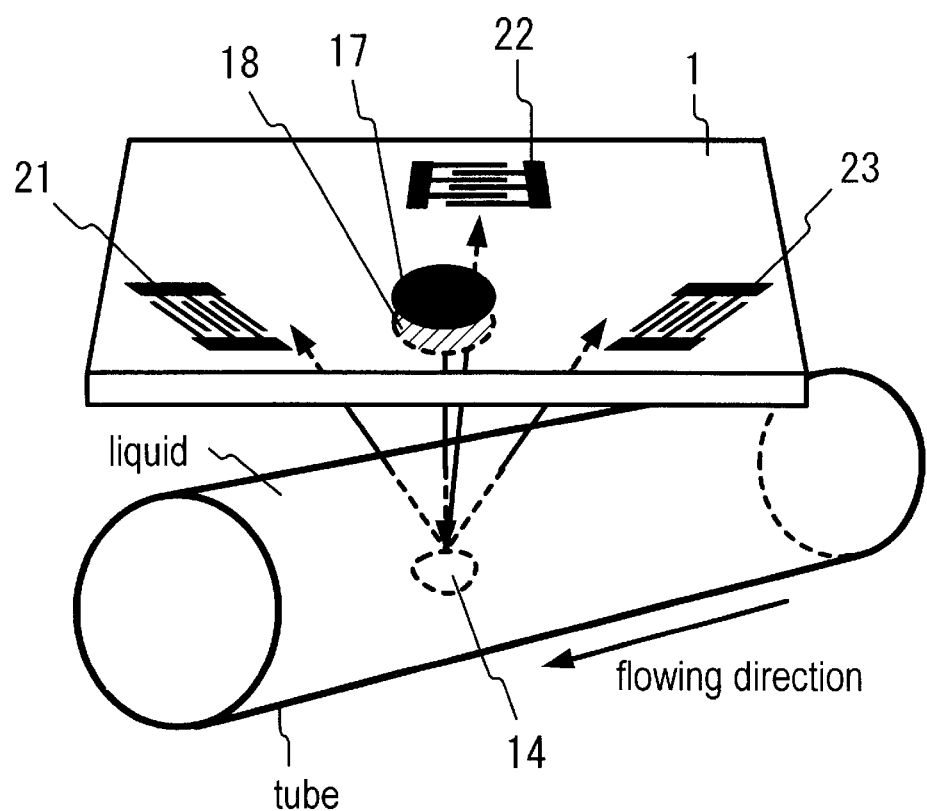
FIG. 25 shows a schematic illustration of an ultrasonic moving-speed measuring system according to a ninth embodiment of the present invention.

FIG. 25 shows a schematic illustration of an ultrasonic moving-speed measuring system according to a ninth embodiment of the present invention. The ultrasonic moving-speed measuring system has the same construction as FIG. 21, except for the absence of first interdigital transducer 19 and second interdigital transducer 20, and the presence of first interdigital transducer 21, second interdigital transducer 22, and third interdigital transducer 23. First interdigital transducer 21, second interdigital transducer 22, and third interdigital transducer 23 have the same electrode patterns as interdigital transducer 4, and are formed on the upper end surface of piezoelectric substrate 1 such that they together make a triangle. In this way, piezoelectric substrate 1, the thickness-vibration mode transducer, first interdigital transducer 21, second interdigital transducer 22, and third interdigital transducer 23 form a transducing assembly. When sensing a flowing speed (S) of a liquid in a tube that exists in a medium, the bottom of the transducing assembly is kept in contact with the medium. In this time, material 14 in the liquid is flowing in accordance with the flowing speed (S) and flowing direction of the liquid.

Figure 26:
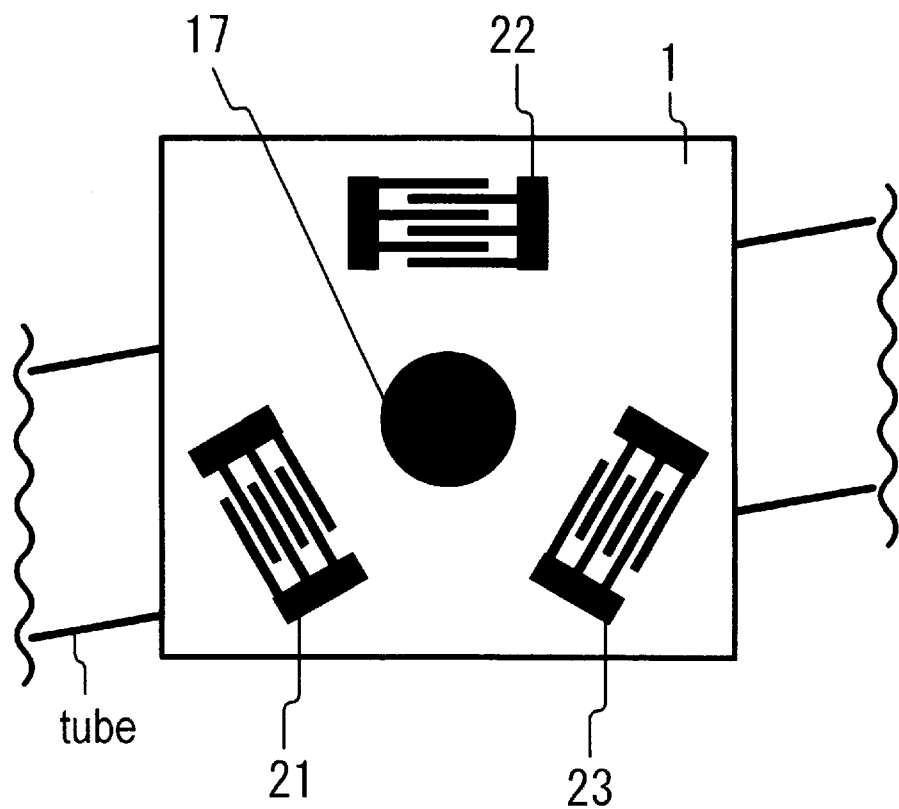
FIG. 26 shows a top plan view of the transducing assembly in FIG. 25 and the tube.

FIG. 26 shows a top plan view of the transducing assembly in FIG. 25 and the tube. Second electrode 18 is not drawn in FIG. 26. It should be noted that a first intersecting line on each finger-center of the finger overlap-zone of first interdigital transducer 21, a second intersecting line on each finger-center of the finger overlap-zone of second interdigital transducer 22, and a third intersecting line on each finger-center of the finger overlap-zone of third interdigital transducer 23 meet one another at the center of first electrode 17.

In the ultrasonic moving-speed measuring system in FIG. 25, when an input electric signal with a carrier frequency ($F_0$) is applied to the thickness-vibration mode transducer composed of first electrode 17 and second electrode 18, a longitudinal wave is radiated into the medium, and then, into the liquid through the tube. If the longitudinal wave is reflected at material 14, a first delayed electric signal with a first Doppler frequency ($F_f$) is detected at first interdigital transducer 21 via a mode conversion from a first reflected longitudinal wave having a reflection angle ($\alpha$) to a first leaky Lamb wave, and a second delayed electric signal with a second Doppler frequency ($F_s$) at second interdigital transducer 22 is detected via a mode conversion from a second reflected longitudinal wave having a reflection angle ($\alpha$) to a second leaky Lamb wave, and then, a third delayed electric signal with a third Doppler frequency ($F_t$) is detected at third interdigital transducer 23 via a mode conversion from a third reflected longitudinal wave having a reflection angle ($\alpha$) to a third leaky Lamb wave. The flowing direction and the flowing speed (S) of the liquid is sensed at signal analyzer 6 in terms of a combination of a first difference between the carrier frequency ($F_0$) and the first Doppler frequency ($F_f$), a second difference between the carrier frequency ($F_0$) and the second Doppler frequency ($F_s$), and a third difference between the carrier frequency ($F_0$) and the third Doppler frequency ($F_t$). In addition, the use of three equivalent interdigital transducers, that is, first interdigital transducer 21, second interdigital transducer 22, and third interdigital transducer 23, cancels a change in circumstances such as temperature, pressure, and so on.

Moreover, in the ultrasonic moving-speed measuring system in FIG. 25, the use of three interdigital transducers 9 shown in FIG. 14, in place of first interdigital transducer 21, second interdigital transducer 22, and third interdigital transducer 23, causes availability for various flowing-speed of the liquid.

Furthermore, if an input electric signal ($E_1$, $E_2$, $E_3$ or $E_4$) with a carrier frequency ($F_{01}$, $F_{02}$, $F_{03}$ or $F_{04}$), respectively, is applied to the thickness-vibration mode transducer composed of first electrode 17 and second electrode 18, a longitudinal wave is radiated into the medium, and then, into the liquid through the tube. When the longitudinal wave is reflected at material 14, a first delayed electric signal with a first Doppler frequency ($F_{f1}$, $F_{f2}$, $F_{f3}$ or $F_{f4}$) is effectively detected at first interdigital transducer 21 via a mode conversion from a first reflected longitudinal wave having a reflection angle ($\alpha_1$, $\alpha_2$, $\alpha_3$ or $\alpha_4$) to a first leaky Lamb wave, and a second delayed electric signal with a second Doppler frequency ($F_{s1}$, $F_{s2}$, $F_{s3}$ or $F_{s4}$) is effectively detected at second interdigital transducer 22 via a mode conversion from a second reflected longitudinal wave having a reflection angle ($\alpha_1$, $\alpha_2$, $\alpha_3$ or $\alpha_4$) to a second leaky Lamb wave, and then, a third delayed electric signal with a third Doppler frequency ($F_{t1}$, $F_{t2}$, $F_{t3}$ or $F_{t4}$) is effectively detected at third interdigital transducer 23 via a mode conversion from a third reflected longitudinal wave having a reflection angle ($\alpha_1$, $\alpha_2$, $\alpha_3$ or $\alpha_4$) to a third leaky Lamb wave. For example, when the longitudinal wave is reflected at material 14, the first delayed electric signal with the first Doppler frequency ($F_{f4}$) is detected at first interdigital transducer 21 via the mode conversion from the first reflected longitudinal wave having a reflection angle ($\alpha_4$) to the first leaky Lamb wave, and the second delayed electric signal with the second Doppler frequency ($F_{s4}$) is detected at second interdigital transducer 22 via the mode conversion from the second reflected longitudinal wave having the reflection angle ($\alpha_4$) to the second leaky Lamb wave, and then, the third delayed electric signal with the third Doppler frequency ($F_{t4}$) is detected at third interdigital transducer 23 via the mode conversion from the third reflected longitudinal wave having the reflection angle ($\alpha_4$) to the third leaky Lamb wave. In this case, the flowing direction and the flowing speed (S) of the liquid is sensed at signal analyzer 6 in terms of a combination of a first difference between the carrier frequency ($F_{04}$) and the first Doppler frequency ($F_{f4}$), a second difference between the carrier frequency ($F_{04}$) and the second Doppler frequency ($F_{s4}$), and a third difference between the carrier frequency ($F_{04}$) and the third Doppler frequency ($F_{t4}$). As a result, setting a carrier frequency $F_{0i}$ (i=1, 2, 3 or 4) according to a distance $D_i$ (i=1, 2, 3 or 4) between the transducing assembly and material 14 makes first interdigital transducer 21 detect the first delayed electric signal with the first Doppler frequency $F_{fi}$ (i=1, 2, 3 or 4) via the mode conversion from the first reflected longitudinal wave with the reflection angle $\alpha_i$ (i=1, 2, 3 or 4) to the first leaky Lamb wave, and second interdigital transducer 22 detect the second delayed electric signal with the second Doppler frequency $F_{si}$ (i=1, 2, 3 or 4) via the mode conversion from the second reflected longitudinal wave with the reflection angle $\alpha_i$ (i=1, 2, 3 or 4) to the second leaky Lamb wave, and then, third interdigital transducer 23 detect the third delayed electric signal with the third Doppler frequency $F_{ti}$ (i=1, 2, 3 or 4) via the mode conversion from the third reflected longitudinal wave with the reflection angle $\alpha_i$ (i=1, 2, 3 or 4) to the third leaky Lamb wave.

Figure 27:
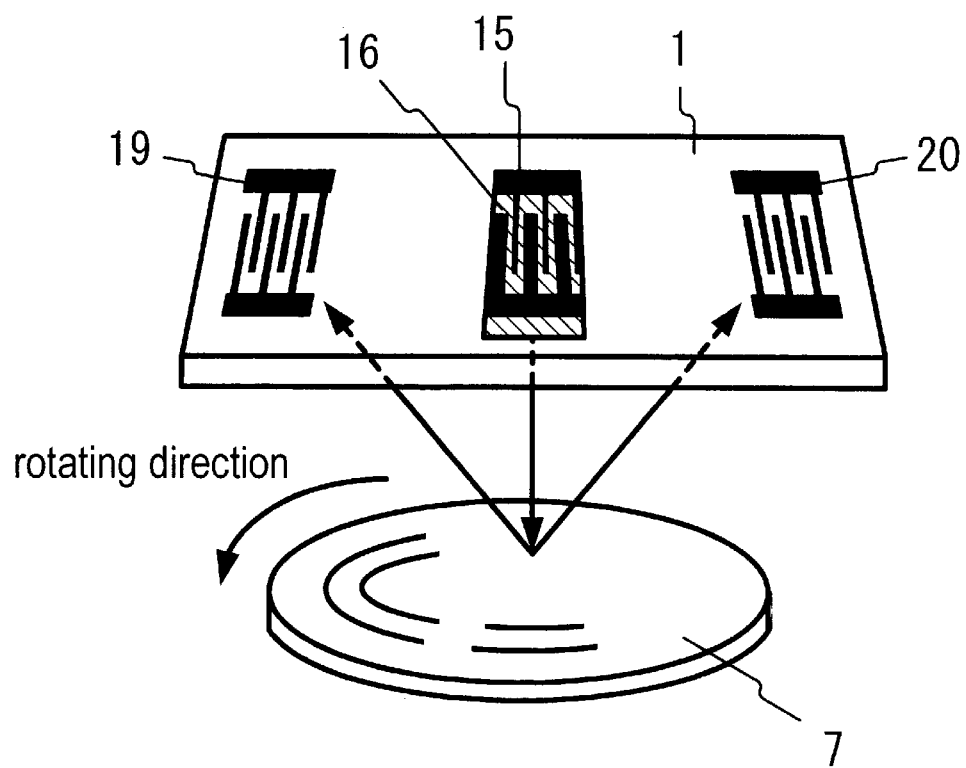
FIG. 27 shows a schematic illustration of an ultrasonic moving-speed measuring system according to a tenth embodiment of the present invention.

FIG. 27 shows a schematic illustration of an ultrasonic moving-speed measuring system according to a tenth embodiment of the present invention. The ultrasonic moving-speed measuring system has the same construction as FIG. 21, except for the presence of interdigital arrangement 15 and second electrode 16 shown in FIG. 19, in place of first electrode 17 and second electrode 18, respectively. Thus, piezoelectric substrate 1, interdigital arrangement 15, second electrode 16, first interdigital transducer 19, and second interdigital transducer 20 form a transducing assembly. When sensing a rotating speed (S) of rotor 7 in water, the bottom of the transducing assembly is kept in contact with water.

Figure 28:
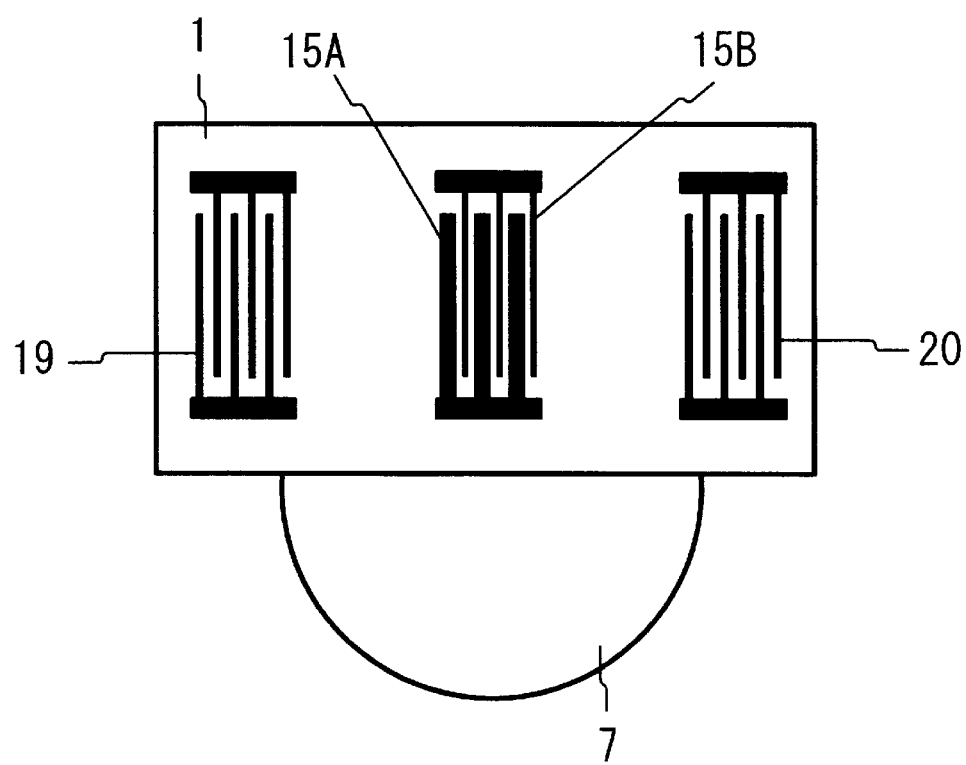
FIG. 28 shows a top plan view of the transducing assembly in FIG. 27 and rotor 7.

FIG. 28 shows a top plan view of the transducing assembly in FIG. 27 and rotor 7. Second electrode 16 is not drawn in FIG. 28. When an input electric signal with a carrier frequency ($F_0$) is applied to the thickness-vibration mode transducer composed of comb-shaped electrode 15A and second electrode 16, a longitudinal wave composed of the main lobe and the grating lobes is effectively radiated into water. If the main lobe of the longitudinal wave is reflected at rotor 7, a first delayed electric signal with a first Doppler frequency ($F_f$) is detected at first interdigital transducer 19 via a mode conversion from a first reflected longitudinal wave having a reflection angle ($\alpha$) to a first leaky Lamb wave, and at the same time, a second delayed electric signal with a second Doppler frequency ($F_s$) is detected at second interdigital transducer 20 via a mode conversion from a second reflected longitudinal wave having a reflection angle ($\alpha$) to a second leaky Lamb wave. In this time, detecting a larger Doppler frequency decides the rotating direction. As a result, the rotating direction and the rotating speed (S) of rotor 7 is sensed at signal analyzer 6 in terms of a difference between the carrier frequency ($F_0$) and a larger one of the first- and second Doppler frequencies ($F_f$ and $F_s$).

In the ultrasonic moving-speed measuring system in FIG. 27, the use of two interdigital transducers 9 shown in FIG. 14, in place of first interdigital transducer 19 and second interdigital transducer 20, causes availability for various-speed rotation of rotor 7.

In the ultrasonic moving-speed measuring system in FIGS. 21, 25 and 27, it is possible to use a counter electrode, which is formed on the lower end surface of piezoelectric substrate 1, and is located at the corresponding position with interdigital transducers 19, 20, 21, 22 and 23, respectively.

Figure 29:
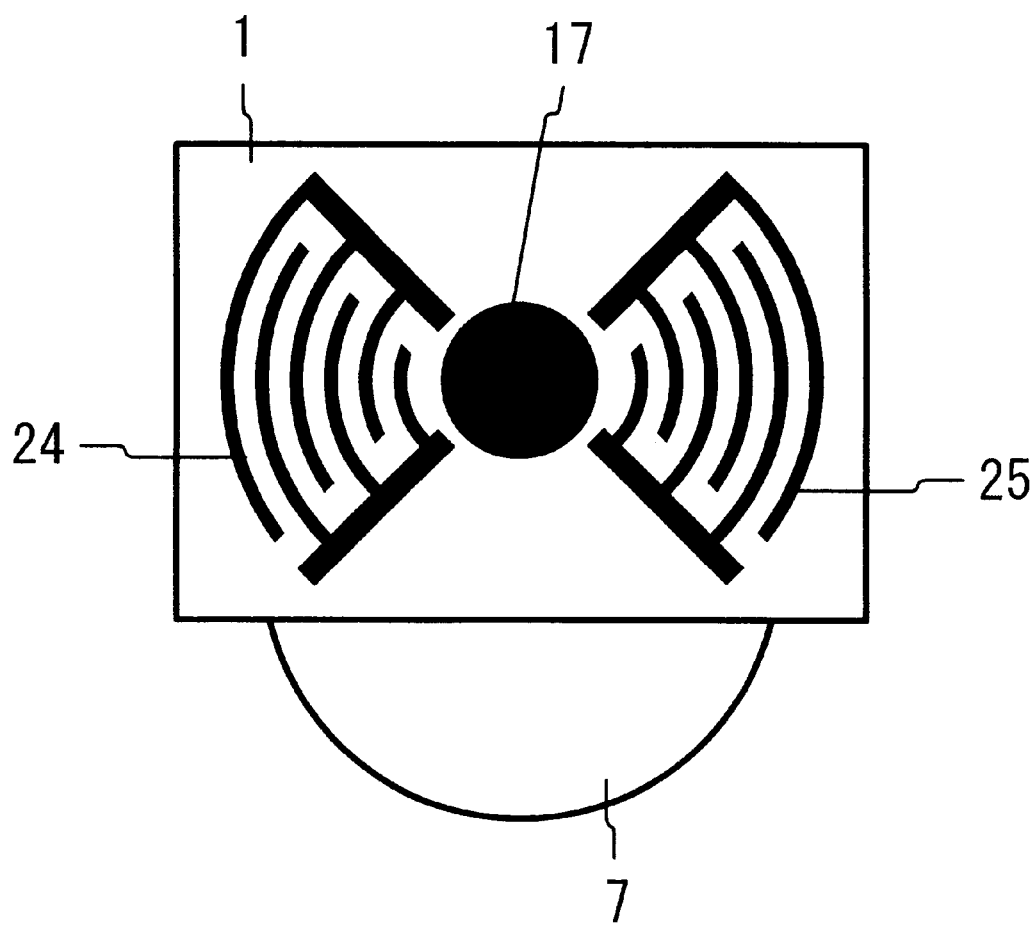
FIG. 29 shows a top plan view of an ultrasonic moving-speed measuring system according to an eleventh embodiment of the present invention.

FIG. 29 shows a top plan view of an ultrasonic moving-speed measuring system according to an eleventh embodiment of the present invention. The ultrasonic moving-speed measuring system has the same construction as FIG. 21, except for the presence of first interdigital transducer 24 and second interdigital transducer 25 in place of first interdigital transducer 19 and second interdigital transducer 20, respectively. First interdigital transducer 24 and second interdigital transducer 25 have the same electrode patterns as interidigital transducer 10 shown in FIG. 15, and have a concentric center at a coincident situation with the center of first electrode 17. In this way, piezoelectric substrate 1, the thickness-vibration mode transducer, first interdigital transducer 24, and second interdigital transducer 25 form a transducing assembly. When sensing a rotating speed (S) of rotor 7 in water, the bottom of the transducing assembly is kept in contact with water. The use of the ultrasonic moving-speed measuring system in FIG. 29 makes the same sensing ability as that in FIG. 21.

In the ultrasonic moving-speed measuring system in FIG. 29, the use of two interdigital transducers 11 shown in FIG. 16, in place of first interdigital transducer 24 and second interdigital transducer 25, causes availability for various-speed rotation of rotor 7.

Figure 30:
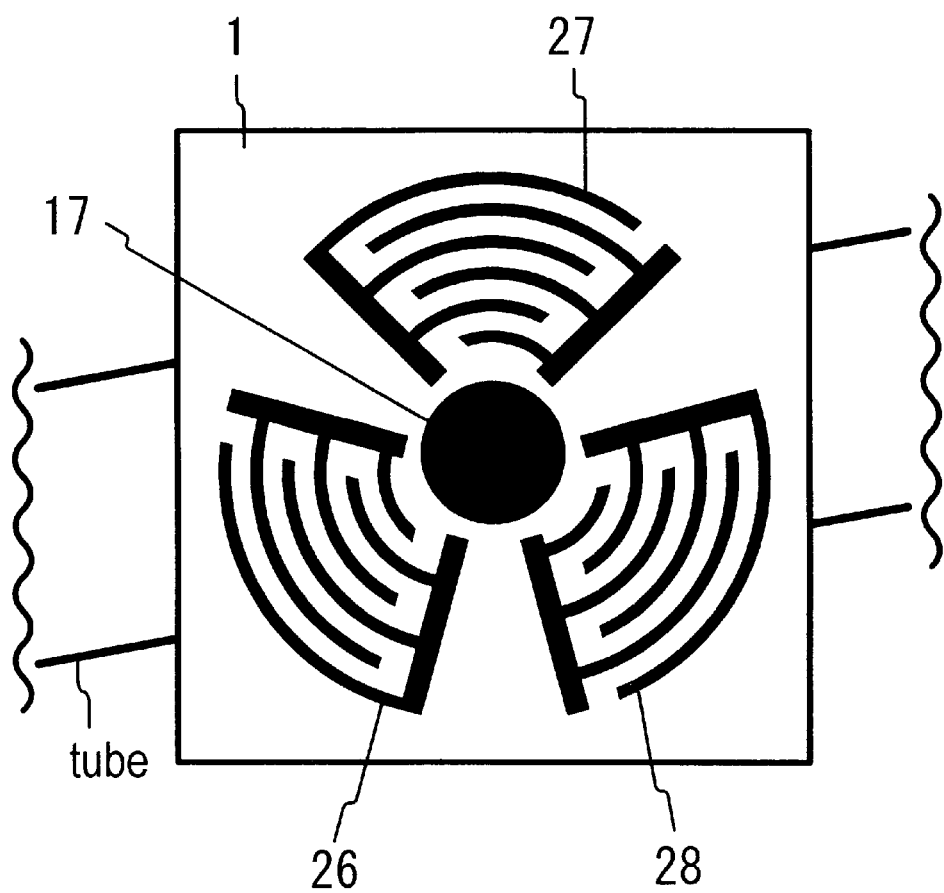
FIG. 30 shows a top plan view of an ultrasonic moving-speed measuring system according to a twelfth embodiment of the present invention.

FIG. 30 shows a top plan view of an ultrasonic moving-speed measuring system according to a twelfth embodiment of the present invention. The ultrasonic moving-speed measuring system has the same construction as FIG. 25, except for the presence of first interdigital transducer 26, second interdigital transducer 27, and third interdigital transducer 28 in place of first interdigital transducer 21, second interdigital transducer 22, and third interdigital transducer 23, respectively. First interdigital transducer 26, second interdigital transducer 27, and third interdigital transducer 28 have the same electrode patterns as interdigital transducer 10 shown in FIG. 15, and have a concentric center at a coincident situation with the center of first electrode 17. Thus, piezoelectric substrate 1, the thickness-vibration mode transducer, first interdigital transducer 26, second interdigital transducer 27, and third interdigital transducer 28 form a transducing assembly. When sensing a flowing speed (S) of a liquid in a tube that exists in a medium, the bottom of the transducing assembly is kept in contact with the medium. In this time, material 14 in the liquid is flowing in accordance with the flowing speed (S) and flowing direction of the liquid. The use of the ultrasonic moving-speed measuring system in FIG. 30 makes the same sensing ability as that in FIG. 25.

In the ultrasonic moving-speed measuring system in FIG. 30, the use of three interdigital transducers 11 shown in FIG. 16, in place of first interdigital transducer 26, second interdigital transducer 27, and third interdigital,transducer 28, causes availability for various flowing-speed of the liquid.

Figure 31:
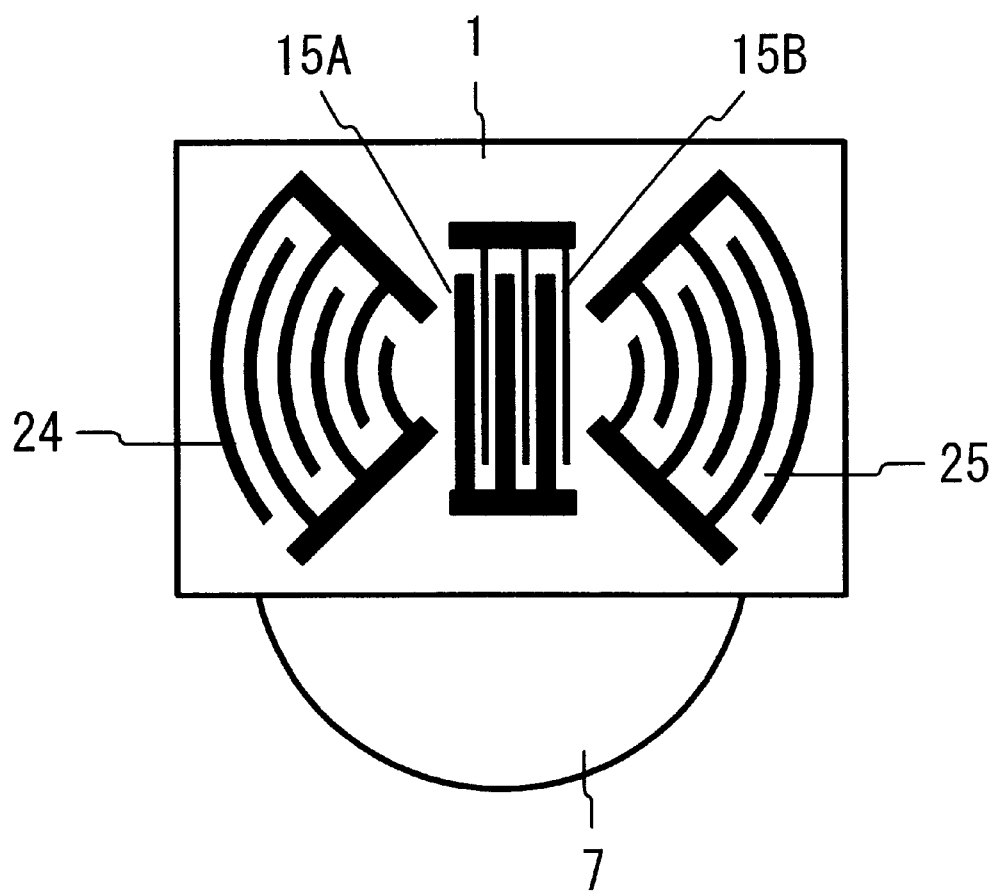
FIG. 31 shows a top plan view of an ultrasonic moving-speed measuring system according to a thirteenth embodiment of the present invention.

FIG. 31 shows a top plan view of an ultrasonic moving-speed measuring system according to a thirteenth embodiment of the present invention. The ultrasonic moving-speed measuring system has the same construction as FIG. 27, except for the presence of first interdigital transducer 24 and second interdigital transducer 25 in place of first interdigital transducer 19 and second interdigital transducer 20, respectively. First interdigital transducer 24 and second interdigital transducer 25 have a concentric center at a coincident situation with the center of interdigital arrangement 15. Thus, piezoelectric substrate 1, interdigital arrangement 15, second electrode 16, first interdigital transducer 24, and second interdigital transducer 25 form a transducing assembly. When sensing a rotating speed (S) of rotor 7 in water, the bottom of the transducing assembly is kept in contact with water. The use of the ultrasonic moving-speed measuring system in FIG. 31 makes the same sensing ability as that in FIG. 27.

In the ultrasonic moving-speed measuring system in FIG. 31, the use of two interdigital transducers 11 shown in FIG. 16, in place of first interdigital transducer 24 and second interdigital transducer 25, causes availability for various-speed rotation of rotor 7.

In the ultrasonic moving-speed measuring system in FIGS. 29, 30 and 31, it is possible to use a counter electrode, which is formed on the lower end surface of piezoelectric substrate 1, and is located at the corresponding position with interdigital transducers 24, 25, 26, 27 and 28, respectively.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. An ultrasonic moving-speed measuring system comprising:

a piezoelectric substrate;

a first electrode formed on an upper end surface of said piezoelectric substrate;

a second electrode formed on a lower end surface of said piezoelectric substrate and located at the corresponding position with said first electrode;

an interdigital transducer formed on said upper end surface of said piezoelectric substrate; and a signal analyzer, said first- and second electrodes forming a thickness-vibration mode transducer, said piezoelectric substrate, said thickness-vibration mode transducer, and said interdigital transducer forming a transducing assembly, said thickness-vibration mode transducer receiving an input electric signal with a carrier frequency approximately equal to the center frequency for operating said thickness-vibration mode transducer, and radiating a longitudinal wave into a medium that is in touch with the bottom of said transducing assembly, and then, making a material in said medium reflect said longitudinal wave back, said interdigital transducer detecting a delayed electric signal with a Doppler frequency via a mode conversion from a reflected longitudinal wave to a leaky Lamb wave, said signal analyzer sensing a moving speed of said material from a difference between said carrier- and Doppler frequencies.

2. An ultrasonic moving-speed measuring system as defined in claim 1, wherein said interdigital transducer has a dispersive electrode-pattern.

3. An ultrasonic moving-speed measuring system as defined in claim 1, wherein said interdigital transducer has an arch-shaped electrode-pattern with a concentric center at a coincident situation with the center of said first electrode.

4. An ultrasonic moving-speed measuring system as defined in claim 1 further comprising a counter electrode formed on said lower end surface of said piezoelectric substrate and located at the corresponding position with said interdigital transducer.

5. An ultrasonic moving-speed measuring system as defined in claim 1 further comprising a signal generator generating an input electric signal $E_i$ (i=1, 2, ..., or n) with a carrier frequency $F_{0i}$ (i=1, 2, ..., or n) in response to a distance $D_i$ (i=1, 2, ..., or n), respectively, between said transducing assembly and said material, in order to make said interdigital transducer detect a delayed electric signal with a Doppler frequency $F_i$ (i=1, 2, ..., or n) via a mode conversion from a reflected longitudinal wave with a reflection angle $\alpha_i$ (i=1, 2, ..., or n), respectively, to a leaky Lamb wave.

6. An ultrasonic moving-speed measuring system as defined in claim 1, wherein said first electrode is made of two comb-shaped electrodes making together an interdigital arrangement, and the ratio of the interdigital periodicity of said interdigital arrangement to the thickness of said piezoelectric substrate is smaller than five times the ratio of the longitudinal wave velocity in said medium to the leaky Lamb wave velocity in said piezoelectric substrate.

7. An ultrasonic moving-speed measuring system as defined in claim 1 further comprising a nonpiezoelectric film, with which said bottom of said transducing assembly is covered.

8. An ultrasonic moving-speed measuring system as defined in claim 1, wherein said piezoelectric substrate is made of a piezoelectric ceramic thin plate, the polarization axis thereof being parallel to the thickness direction thereof.

9. An ultrasonic moving-speed measuring system as defined in claim 1, wherein said piezoelectric substrate is made of a piezoelectric polymer film.

10. An ultrasonic moving-speed measuring system as defined in claim 1, wherein said piezoelectric substrate is made of a piezoelectric single crystal.

11. An ultrasonic moving-speed measuring system comprising:
a piezoelectric substrate;
a first interdigital transducer formed on an upper end surface of said piezoelectric substrate;
a second interdigital transducer having the same electrode pattern as said first interdigital transducer and formed on said upper end surface of said piezoelectric substrate;
a first electrode formed on said upper end surface of said piezoelectric substrate and located between said first- and second interdigital transducers;
a second electrode formed on a lower end surface of said piezoelectric substrate and located at the corresponding position with said first electrode; and
a signal analyzer,
said first- and second electrodes forming a thickness-vibration mode transducer,
said piezoelectric substrate, said thickness-vibration mode transducer, and said first- and second interdigital transducers forming a transducing assembly,
said thickness-vibration mode transducer receiving an input electric signal with a carrier frequency approximately equal to the center frequency for operating said thickness-vibration mode transducer, and radiating a longitudinal wave into a medium that is in touch with the bottom of said transducing assembly, and then, making a material in said medium reflect said longitudinal wave back,
said first interdigital transducer detecting a first delayed electric signal with a first Doppler frequency via a mode conversion from a first reflected longitudinal wave to a first leaky Lamb wave,
said second interdigital transducer detecting a second delayed electric signal with a second Doppler frequency via a mode conversion from a second reflected longitudinal wave to a second leaky Lamb wave,
said signal analyzer sensing a moving direction and a moving speed of said material from a difference between said carrier frequency and a larger one of said first- and second Doppler frequencies.

12. An ultrasonic moving-speed measuring system as defined in claim 11, wherein an intersecting line on each finger-center of the finger overlap-zone of said first interdigital transducer and that of said second interdigital transducer overlap each other.

13. An ultrasonic moving-speed measuring system as defined in claim 11, wherein said first- and second interdigital transducers have a dispersive electrode-pattern, respectively.

14. An ultrasonic moving-speed measuring system as defined in claim 11, wherein said first- and second interdigital transducers have an arch-shaped electrode-pattern, respectively, and make a pair with a concentric center at a coincident situation with the center of said first electrode.

15. An ultrasonic moving-speed measuring system as defined in claim 11 further comprising:
a first counter electrode formed on said lower end surface of said piezoelectric substrate and located at the corresponding position with said first interdigital transducer; and
a second counter electrode formed on said lower end surface of said piezoelectric substrate and located at the corresponding position with said second interdigital transducer.

16. An ultrasonic moving-speed measuring system as defined in claim 11 further comprising a signal generator generating an input electric signal $E_i$ (i=1, 2, ..., or n) with a carrier frequency $F_{0i}$ (i=1, 2, ..., or n) in response to a distance $D_i$ (i=1, 2, ..., or n), respectively, between said transducing assembly and said material, in order to make
said first interdigital transducer detect a first delayed electric signal with a first Doppler frequency $F_{fi}$ (i=1, 2, ..., or n) via a mode conversion from a first reflected longitudinal wave with a reflection angle $\alpha_i$ (i=1, 2, ..., or n) to a first leaky Lamb wave, and then to make
said second interdigital transducer detect a second delayed electric signal with a second Doppler frequency $F_{si}$ (i=1, 2, ..., or n) via a mode conversion from a second reflected longitudinal wave with said reflection angle $\alpha_i$ to a second leaky Lamb wave.

17. An ultrasonic moving-speed measuring system comprising:
a piezoelectric substrate;
a first interdigital transducer;
a second interdigital transducer;
a third interdigital transducer, said first-, second-, and third interdigital transducers having the same electrode patterns as one another, and formed on said upper end surface of said piezoelectric substrate such that they together make a triangle;
a first electrode formed among said first-, second-, and third interdigital transducers on said upper end surface of said piezoelectric substrate;
a second electrode formed on a lower end surface of said piezoelectric substrate and located at the corresponding position with said first electrode; and
a signal analyzer,
said first- and second electrodes forming a thickness-vibration mode transducer,
said piezoelectric substrate, said thickness-vibration mode transducer, and said first-, second- and third interdigital transducers forming a transducing assembly,
said thickness-vibration mode transducer receiving an input electric signal with a carrier frequency in a frequency band-width of ±6 dB from the center frequency for operating said thickness-vibration mode transducer, and radiating a longitudinal wave into a medium that is in touch with the bottom of said transducing assembly, and then, making a material in said medium reflect said longitudinal wave back, said first interdigital transducer detecting a first delayed electric signal with a first Doppler frequency via a mode conversion from a first reflected longitudinal wave to a first leaky Lamb wave, said second interdigital transducer detecting a second delayed electric signal with a second Doppler frequency via a mode conversion from a second reflected longitudinal wave to a second leaky Lamb wave, said third interdigital transducer detecting a third delayed electric signal with a third Doppler frequency via a mode conversion from a third reflected longitudinal wave to a third leaky Lamb wave, said signal analyzer sensing a moving direction and a moving speed of said material from a combination of a first difference between said carrier- and first Doppler frequencies, a second difference between said carrier- and second Doppler frequencies, and a third difference between said carrier- and third Doppler frequencies.

18. An ultrasonic moving-speed measuring system as defined in claim 17, wherein a first intersecting line on each finger-center of the finger overlap-zone of said first interdigital transducer, a second intersecting line on each finger-center of the finger overlap-zone of said second interdigital transducer, and a third intersecting line on each finger-center of the finger overlap-zone of said third interdigital transducer meet one another at the center of said first electrode.

19. An ultrasonic moving-speed measuring system as defined in claim 17, wherein said first-, second-, and third interdigital transducers have a dispersive electrode-pattern, respectively.

20. An ultrasonic moving-speed measuring system as defined in claim 17, wherein said first-, second-, and third interdigital transducers have an arch-shaped electrode-pattern, respectively, and make a set with a concentric center at a coincident situation with the center of said first electrode.

21. An ultrasonic moving-speed measuring system as defined in claim 17 further comprising:

a first counter electrode formed on said lower end surface of said piezoelectric substrate and located at the corresponding position with said first interdigital transducer;

a second counter electrode formed on said lower end surface of said piezoelectric substrate and located at the corresponding position with said second interdigital transducer; and a third counter electrode formed on said lower end surface of said piezoelectric substrate and located at the corresponding position with said third interdigital transducer.

22. An ultrasonic moving-speed measuring system as defined in claim 17 further comprising a signal generator generating an input electric signal $E_i$ (i=1, 2, ..., or n) with a carrier frequency $F_{0i}$ (i=1, 2, ..., or n) in response to a distance $D_i$ (i=1, 2, ..., or n), respectively, between said transducing assembly and said material, in order to make said first interdigital transducer detect a first delayed electric signal with a first Doppler frequency $F_{fi}$ (i=1, 2, ..., or n) via a mode conversion from a first reflected longitudinal wave with a reflection angle $\alpha_1$ (i=1, 2, ..., or n) to a first leaky Lamb wave, and to make said second interdigital transducer detect a second delayed electric signal with a second Doppler frequency $F_{si}$ (i=1, 2, ..., or n) via a mode conversion from a second reflected longitudinal wave with said reflection angle $\alpha_i$ to a second leaky Lamb wave, and then, to make said third interdigital transducer detect a third delayed electric signal with a third Doppler frequency $F_{ti}$ (i=1, 2, ..., or n) via a mode conversion from a third reflected longitudinal wave with said reflection angle $\alpha_i$ to a third leaky Lamb wave.

\* \* \* \* \*